(12) United States Patent
Yuan et al.

(10) Patent No.: US 12,029,532 B2
(45) Date of Patent: Jul. 9, 2024

(54) BLOOD PRESSURE MEASURING DEVICE AND METHOD

(71) Applicant: ViviPulse, LLC, New Haven, CT (US)

(72) Inventors: Paul Yuan, Burlingame, CA (US); Zhen Li, San Diego, CA (US)

(73) Assignee: VIVIPULSE, LLC, New Haven, CT (US)

( * ) Notice: Subject to any disclaimer, the term of this patent is extended or adjusted under 35 U.S.C. 154(b) by 0 days.

(21) Appl. No.: 18/140,008

(22) Filed: Apr. 27, 2023

(65) Prior Publication Data

US 2023/0263410 A1 Aug. 24, 2023

Related U.S. Application Data

(62) Division of application No. 16/653,577, filed on Oct. 15, 2019, now Pat. No. 11,642,034.

(60) Provisional application No. 62/744,896, filed on Oct. 12, 2018.

(51) Int. Cl.
*A61B 5/02* (2006.01)
*A61B 5/00* (2006.01)
*A61B 5/021* (2006.01)

(52) U.S. Cl.
CPC ............ *A61B 5/021* (2013.01); *A61B 5/0077* (2013.01); *A61B 5/6826* (2013.01); *A61B 5/7405* (2013.01); *A61B 5/742* (2013.01); *A61B 5/7455* (2013.01); *A61B 5/7475* (2013.01); *A61B 2562/0238* (2013.01); *A61B 2562/0247* (2013.01)

(58) Field of Classification Search
CPC .... A61B 2562/0238; A61B 2562/0247; A61B 2562/0252; A61B 5/0022; A61B 5/0075; A61B 5/0077; A61B 5/02007; A61B 5/021; A61B 5/02208; A61B 5/02241; A61B 5/1172; A61B 5/14542; A61B 5/1495; A61B 5/6826; A61B 5/7264; A61B 5/7405; A61B 5/742; A61B 5/7455; A61B 5/7475; G16H 40/67; G16H 50/20

See application file for complete search history.

(56) References Cited

U.S. PATENT DOCUMENTS

| | | | |
|---|---|---|---|
| 7,539,532 B2 * | 5/2009 | Tran | A61B 5/1112 600/509 |
| 7,695,440 B2 * | 4/2010 | Kondo | A61B 5/6838 600/500 |
| 8,574,161 B2 * | 11/2013 | Banet | A61B 5/021 600/493 |

* cited by examiner

*Primary Examiner* — Mark D Remaly
(74) *Attorney, Agent, or Firm* — McCormick, Paulding & Huber PLLC

(57) ABSTRACT

Blood pressure detection apparatuses and methods for detecting a blood pressure of a user are described comprising optical sensors/detectors and a force sensor and, in some embodiments, comprising only a force sensor, measuring force applied by a finger. Blood pressure is measured by applying an increasing (or decreasing) force or pressure with a finger of the user on at least the force sensor, which, in some embodiments, may be a plurality of increasing pressure steps, each step being held within a predetermined acceptable pressure/force tolerance range for a predetermined hold time, and measuring the force applied by the finger and, in some embodiments, optically measuring the blood in a vessel in the finger relating to the applied pressure/force. Feedback (visual, haptic, sound) of the applied pressure is provided to the user.

20 Claims, 23 Drawing Sheets

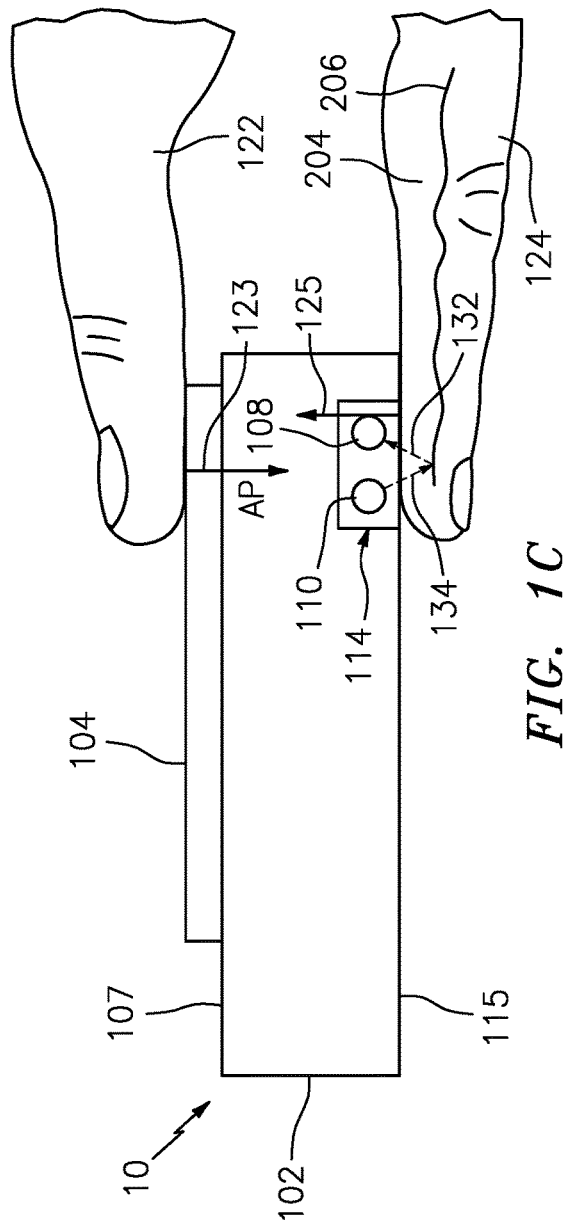
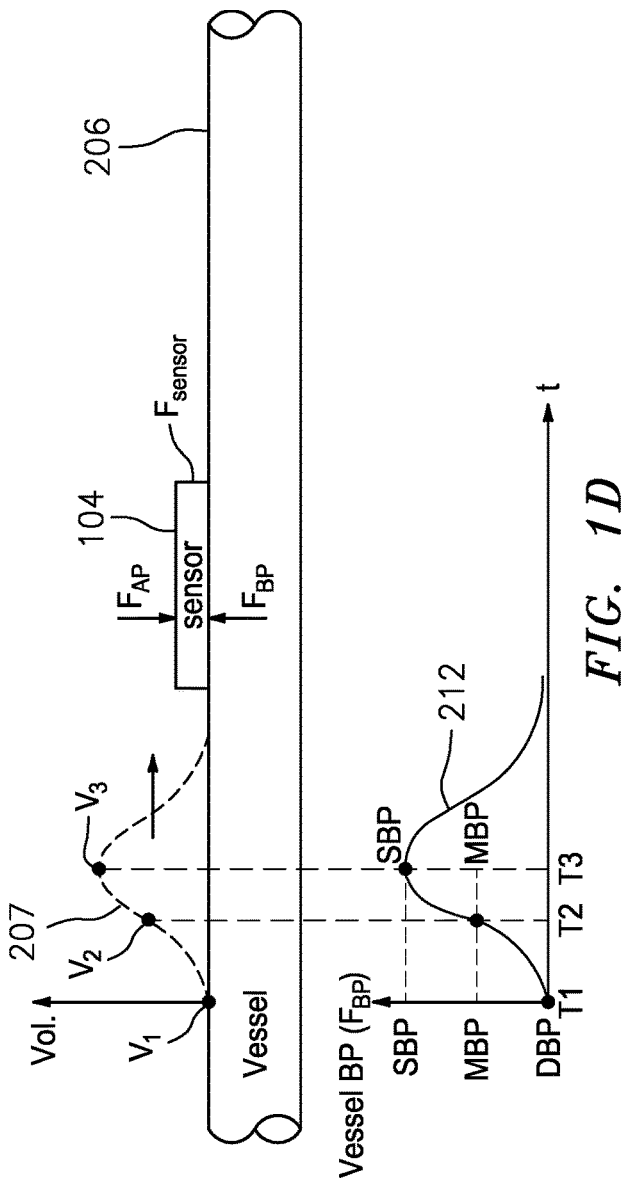
FIG. 1C
FIG. 1D

BLOOD PRESSURE MEASURING DEVICE AND METHOD

CROSS REFERENCES TO RELATED APPLICATIONS

This application is a divisional of U.S. application Ser. No. 16/653,577, filed Oct. 15, 2019, which claims the benefit of U.S. Provisional Patent Application Ser. No. 62/744,896, filed Oct. 12, 2018, the entire disclosure of which is incorporated herein by reference to the fullest extent permitted by applicable law.

BACKGROUND

Blood pressure may be understood to be the expanding force per blood vessel area, exerted by the blood as it flows through the vessel. With each heartbeat, the blood flow changes as the heart contracts and dilates, thus the blood pressure oscillates accordingly. The maximal and minimal blood pressure in this oscillation is designated as systolic and diastolic blood pressure, respectively.

Conventional blood pressure measuring devices and methods obtain a blood pressure reading of a patient by securing a cuff device to an arm of the patient, inflating (tightening) the cuff device until an artery of the patient is compressed such that no blood may pass and deflating (loosening) the cuff device so that blood may resume flow through the artery while listening to detect the pressure at which blood resumes flow. Typically, these conventional methods are performed by a medical provider. Such conventional devices may be bulky and/or difficult to use by the patient alone.

BRIEF DESCRIPTION OF THE DRAWINGS

FIG. 1C is a side view of the blood pressure measuring device of FIG. 1A being held by a user in accordance with embodiments of the present disclosure.

FIG. 1D is an illustration of the operation of a force sensor of the blood pressure measuring device shown in FIG. 1A in connection with a blood vessel of a user in accordance with embodiments of the present disclosure.

DETAILED DESCRIPTION

Under normal conditions, the expanding force generated by blood is balanced by the vessel elasticity. When external force (or pressure) is applied, however, the blood vessel will deform depending on the amount of applied force, according to the following known relationship:

| External pressure level | Blood flow |
| --- | --- |
| External pressure <= diastolic blood pressure | No change |
| Diastolic blood pressure < external pressure < systolic blood pressure | Vessel starts to deform and blood flow decreases as external pressure increases |
| External pressure >= systolic blood pressure | Vessel collapse and no blood flow |

Based on this relationship, one can measure the blood pressure with a blood pressure measurement (or detection) device (or apparatus) by measuring the change of blood flow in relation to an external pressure source.

Figure 1A:
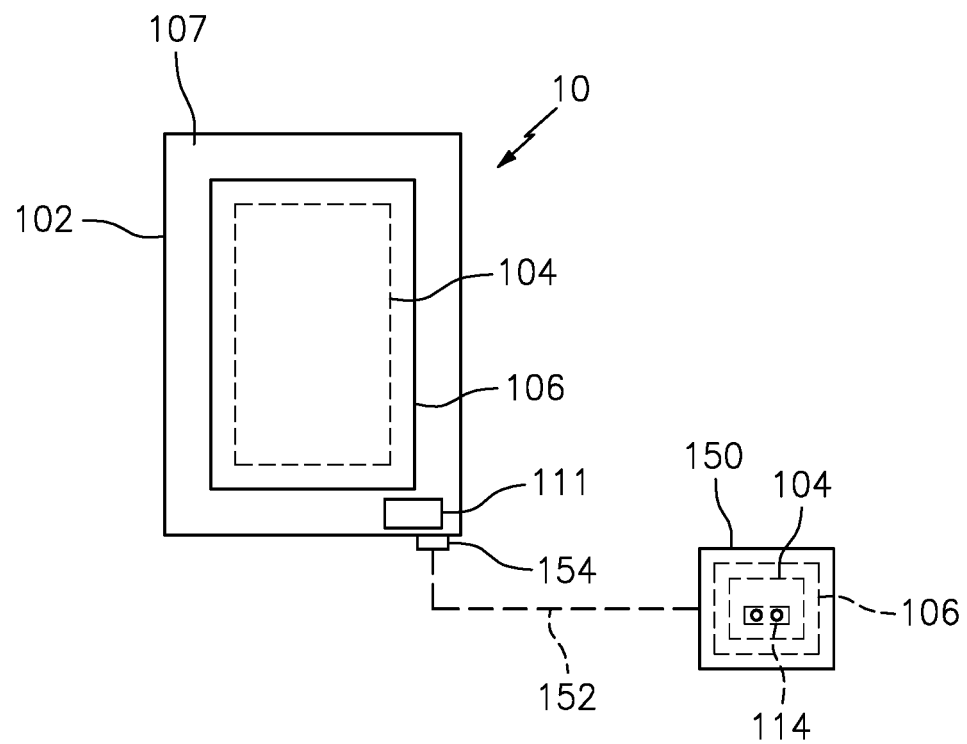
FIG. 1A is a front (or top) view of an exemplary blood pressure measuring device and an optional separate sensing device, in accordance with embodiments of the present disclosure.
Figure 1B:
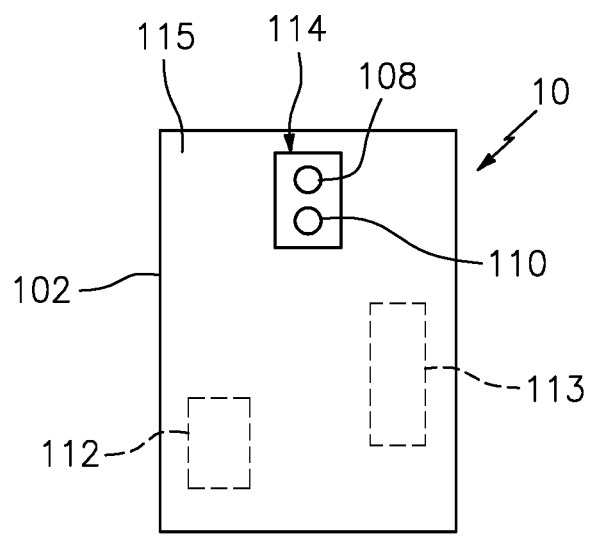
FIG. 1B is a rear (or bottom) view of the blood pressure measuring device of FIG. 1A in accordance with embodiments of the present disclosure.

Referring to FIGS. 1A-1C, a blood pressure measurement (BPM) or BP measurement device or apparatus 10 according to embodiments of the present disclosure comprises a frame body (or housing) 102 and a force sensor 104 (or pressure sensor) arranged beneath a display screen 106 on a front face (or first side) 107 of the BPM device 10. The BPM device 10 comprises a light (or optical) source 108 and an optical sensor 110 on a rear face (or second side) 115 (FIG. 1B) of the apparatus 10. The BPM device 10 may have a speaker 111 configured to generate audio notifications and/or a haptic element 113 (e.g., a vibration transducer) configured to generate haptic, tactic or vibrational notifications or feedback to a user. The force sensor 104, display screen 106, light source 108, optical sensor 110, speaker 111 and haptic element 113 may be operatively connected to a controller 112 (e.g., a computer-based controller) contained within the frame body 102 of the apparatus 10. The force sensor 104 may be any force sensor having sufficient sensitivity, range and bandwidth/fidelity to perform the functions described herein.

The terms "force" and "pressure" may be sued interchangeably herein. However, it is to be understood by those skilled in the art that pressure equals force over a specified area (P=F/A).

The force sensor 104 is configured to detect various levels of an applied force (or applied pressure AP) as well as changes of force level in the applied force. The force sensor 104 and display screen 106 are configured so that a user can apply (or exert) a force anywhere on the display screen 106 and the force sensor 104 can detect the applied force. The display screen 106 may optionally be configured to display a real-time indicator of the amount of force being applied to the display screen 106 (discussed more hereinafter).

The light source 108 and the optical sensor 110 may be collectively referred to herein as an optical source/sensor arrangement 114, are arranged substantially near each other so that an appendage of a user, such as a finger 124 (FIG. 1C), covers at least a portion of the light source 108 and at least a portion of the optical sensor 110 simultaneously. For the purposes of the present disclosure, a finger refers to a digit of a hand of a user including the thumb. Although the surface area of the finger 124 may vary by user, a person of ordinary skill in the art would understand how to arrange the light source 108 and optical sensor 110 sufficiently close to each other such that the finger 124 of most users could simultaneously cover both portions of the light source 108 and optical sensor 110 to allow the light source 108 to illuminate 132 a vein (or vessel or blood vessel) 130 in the finger 124 and the optical sensor 110 to detect the reflected light 134. The light source 108 may be virtually any type of light generating element, such as a light emitting diode ("LED"). For example, the light source 108 may be configured as a green LED. Other colors may be used if desired provided it provides the function and performance described herein.

In some embodiments, in operation, a user pinches the BPM device 10 with two or more fingers 122, 124. A first finger 122 (e.g., a thumb) pinches the BPM device 10 at the front face where the force sensor 104 and display screen 106 (or force-sensitive or pressure-sensitive screen) are arranged, and a second (opposing) finger (e.g., index finger, middle finger, ring finger, or little/pinky finger) pinches the apparatus 10 at the rear face where the light source 108 and optical sensor 110 are arranged. Other fingers may be used if desired for the two positions. Also, the fingers may be from different hands if desired, i.e., thumb from right hand and index finger from left hand (or vise versa). However, it is likely easiest to use two opposing fingers on the same hand and preferably a thumb on the screen and other finger on the optical source/sensor 108/110 using a pinching action (discussed below).

The user applies opposing pressure 123, 125 against the device 10 by pinching (or using a pincer action) with fingers 122, 124 at a first force level for a first predetermined duration of time (or hold time). For example, the user applies pressure by pinching at a first force level for a predetermined hold time, e.g., at least about three, about four or about five seconds. Other times may be used if desired. Other pinch hold times are within the scope of the present disclosure provided the hold time is long enough for the controller to read enough data points to obtain the desired measurement(s). After the first hold time, the user applies pressure at a second force level for a second hold time, the second force level being greater than the first force level. The user may perform this pinching procedure a plurality of times. For example, the user may conduct five iterations of this process, i.e., applying pressure at five different force levels for five hold times. The predetermined hold times may be the same length of time or different lengths of time. The procedure of pinching at different force levels (or stages or steps) may be referred to generally as a "pinching process." It is within the scope of the present disclosure for the pinching process to be performed any number of times sufficient to provide the desired BP measurement. For example, the user can apply pressure for about three (3) seconds at seven (7) different force levels, or for about five (5) seconds at seven (7) force levels, or about three (3) seconds at five (5) different force levels, or for about five (5) seconds at five (5) force levels, or any other number of seconds and number of force levels provided sufficient data can be taken to conduct the necessary calculations disclosed herein to determine the user's blood pressure.

Also, as discussed herein, each of the pressure levels have a tolerance to hold the pressure within a predetermined acceptable force or pressure range or tolerance, e.g., +/−X force units (e.g., +/−0.5 force units), as measured by the pressure/force sensor in the device for a given pressure or force level. Such force units may be converted to pressure in psi or mm Hg using Eq. 2 herein, if desired. Other ranges may be used if desired. The acceptable pressure range (or tolerance) may be the same for all pressure levels or change based on the pressure levels if needed to obtain the desired BP measurement accuracy. For example, the target or acceptable pressure range for pressure steps 1 to 4 may be /−1 mmHg, and the acceptable pressure range for pressure steps 5 to 7 may be /−0.5 mmHg. Also, in some embodiments, the measurement hold time does not need to be continuous as long as the total hold time for that pressure level is met. For example, if the predetermined hold time is 5 seconds for a given pressure level, the user may apply the pressure for 3 seconds within the pressure range, and then move out of the range, and then back into the range, as long as the total time in the range is 5 seconds, the reading may be sufficient.

The BPM device 10 may be optionally configured to instruct the user (e.g., via notification, alert, or feedback) when to proceed to the next (or greater) level of applied force through pinching. For example, the apparatus 10 may generate an audio notification through the speaker 111, a visual notification on the display screen 106 and/or a tactile notification through the haptic element 113 such as a vibration, or any combination thereof.

While the first (or top) finger 122 (e.g., thumb) of the user is applying pressure 123 at the front face 107 at the pressure sensor 104 of the BPM device 10, the second finger 124 applies force the rear face 115 of the apparatus 10 and is covering the light source 108 and optical sensor 110. During each iteration of the pinching process at different force levels, the light source 108 is activated to provide a source of light 132 and the optical sensor 110 is detecting light 134 returned (or reflected) from the user's second finger. For example, the light source 108 may be activated to be continuously emitting the source light 132. The optical sensor 110 transmits an electrical signal to the controller 112 based on the intensity of light 134 detected by the optical sensor 110. The optical sensor 110 is configured to detect light a detection frequency. For example, the electrical signal from the optical sensor 110 is sampled by an analog to digital (A/D) converter in the controller at a predetermined sample rate, e.g., 30 Hz (or 30 samples/second). Other sample rates may be used, if desired, provided the sample rate provides the function and performance described herein.

Referring to FIG. 1D, an illustration shows the force sensor 104 (FIG. 1A) being used in connection with a vein 130 (or blood vessel) of a finger 124 (FIG. 1C) of the user. As a pressure pulse 136 from the user's heartbeat moves through the vein 130, blood volume in the vein (or vessel) 130 will increase. At time $T_1$, the blood volume in the vein 130 will be equal to $V_1$, which is equal to the diastolic blood pressure (DBP). At time $T_2$, the blood volume in the vein 130 will be equal to $V_2$, which is equal to the mean blood pressure (MBP) of the user. At time $T_3$, the blood volume in the vein 130 will be equal to $V_3$, which is equal to the systolic blood pressure (SBP) of the user.

Figure 2A:
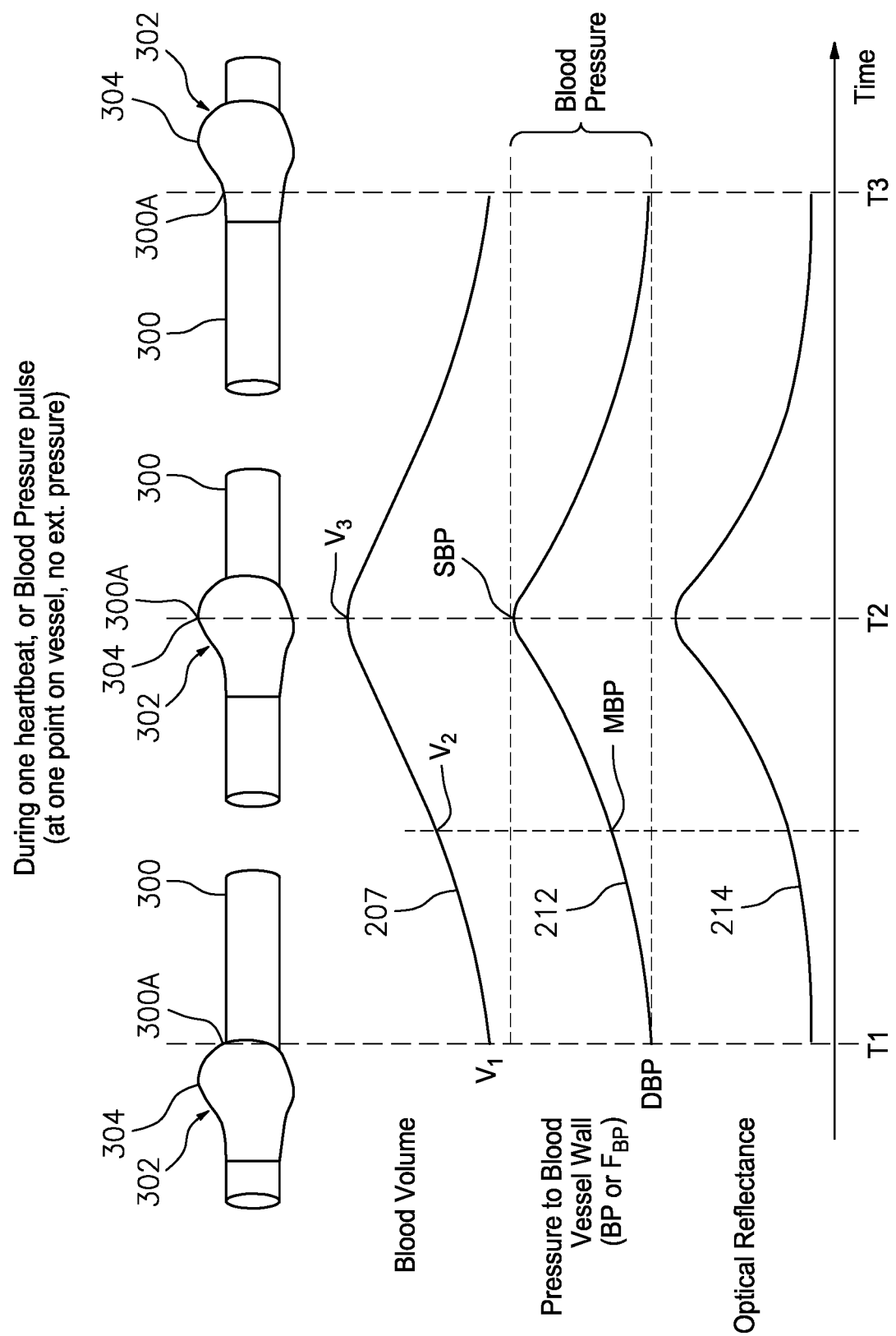
FIG. 2A illustrates blood volume, pressure pulse wave and optical reflectance data collected by a blood pressure measuring device and correlated with a single heartbeat in accordance with embodiments of the present disclosure.

Referring to FIG. 2A, normalized illustrative curves showing values for instantaneous blood volume 207, pressure to blood vessel wall (pulse wave) detected values 212 and optical reflectance 214 detected values corresponding with different portions of one heartbeat pressure wave travelling through a blood vessel 300 when no applied pressure is being exerted by the user on the blood vessel 300, or by any other external pressure. The curves 207, 212, and 214, are shown for illustrative purposes to illustrate the general trends and minimum and maximum values of the respective parameters shown and are not to scale. When the blood volume 207, pressure to blood vessel wall (or pulse wave) 212 and optical reflectance 214 values are at an initial minimum, those values can be correlated with a time $T_1$ when a pressure bulge 302 in the user's blood vessel 300 due to the heartbeat pressure wave is just entering a blood vessel location 300A. When the blood volume 207, pressure to blood vessel wall 212 and optical reflectance 214 values are an absolute maximum (or peak), they can be correlated with a time $T_2$ when the maximum pressure of the pressure bulge 302 is at the blood vessel location 300A. And when the blood volume 207, pressure pulse wave 212 and optical reflectance 214 values descend to another absolute minimum, those values can be correlated with a time $T_3$ when the pressure bulge 302 is just exiting the blood vessel location 300A. Both the optical signal detected values 214 and the pressure signal detected values 212 show the same underlying hemodynamic change in the blood vessel 300.

Figure 2B:
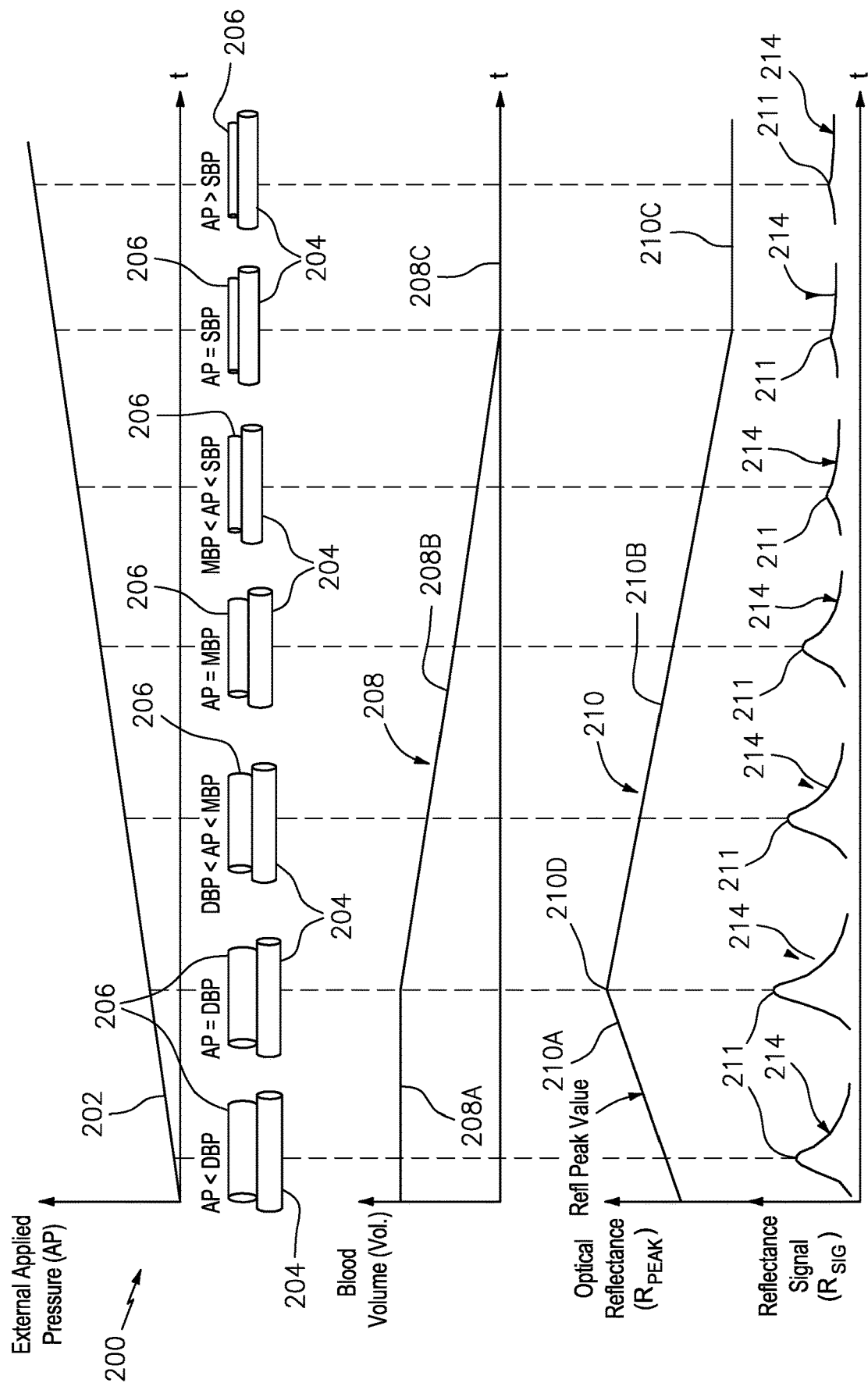
FIG. 2B illustrates tissue and a blood vessel of a finger of a user at various stages of compression (or applied pressure AP) with accompanying blood volume, optical reflectance and pulse wave graphs in accordance with embodiments of the present disclosure.

Referring to FIG. 2B, a graph 200 illustrates various levels of pinching compression force or the user's first finger 124 and/or second finger 122 undergoes as the applied pressure ("AP") 202 increases when the user pinches the BPM device 10. When the first finger 124 and/or second finger 122 initially comes into contact with the BPM device 10, there is substantially no compression of the tissue 204 or the blood vessel 206 contained within the tissue 204 because the applied pressure AP 202 is less than the diastolic blood pressure ("DBP") (AP<DBP). When the applied pressure 202 is equal to the diastolic blood pressure (AP=DBP) of the patient (or user), the tissue 204 is compressed slightly, but the blood vessel 206 is not compressed. When the applied pressure 202 is greater than the diastolic blood pressure but less than the mean (or average) blood pressure ("MBP") (DBP<AP<MBP), the blood vessel 206 is compressed slightly, but the tissue 204 is not substantially more compressed. When the applied pressure 202 is equal to the mean blood pressure (AP=MBP, where MBP=(DBP+SBP)/2), the blood vessel 206 is further compressed. When the applied pressure 202 is greater than the mean blood pressure and less than the systolic blood pressure ("SBP") (MBP<AP<SBP), the blood vessel 206 is further compressed. When the applied pressure 202 is equal to the systolic blood pressure (AP=SBP), the blood vessel 206 is further compressed such that the blood vessel 206 is in a collapsed condition where blood is unable to flow through the blood vessel 206 at the point of compression. When the applied pressure 202 is greater than the systolic blood pressure (SBP<AP), the blood vessel 206 does not substantially compress further since the blood vessel 206 is in a collapsed condition and blood is unable to flow through the blood vessel 206 at the point of compression.

Since the blood vessel 206 does not compress when the applied pressure 202 is less than or equal to the diastolic blood pressure, the blood volume 208 remains substantially constant as shown by a section 208A of the blood volume curve 208. Since the blood vessel 206 compresses when the applied pressure 202 is greater than diastolic blood pressure up to the systolic blood pressure, the blood volume 208 decreases with increasing applied pressure 202 as shown by a section 208B of the curve 208. Since the blood vessel 206 is in a collapsed condition when the applied pressure 202 is equal to or greater the systolic blood pressure, the blood volume 208 remains constant for applied pressure 202 greater than or equal to the systolic blood pressure as shown by section 208C of the curve 208.

The optical reflectance of light (or the reflected light 134) returned from a user's finger 124 (FIG. 1C) is related to the blood volume 208 contained in the blood vessel 206. The optical reflectance plot 210 shown in FIG. 2B is plotted with respect to applied pressure 202 and based on values of the reflected light 134 detected at the optical sensor 110 (FIGS. 1B and 1C). The optical reflectance plot 210 values substantially correspond with the blood volume curve 208 in the blood vessel 206 at the applied pressure 202. However, we have found that the optical reflectance 210 detected at the optical sensor 110 (FIG. 1B) initially increases as applied pressure 202 increases as shown by section 210A until the applied pressure 202 is equal to the diastolic blood pressure (DBP) even though there is no change in blood volume 208. The detected optical reflectance 210 increases initially at least because the optical sensor 110 (FIG. 1B) is able to detect more returned (or reflected) light 134 as the tissue 204 compresses even though the blood volume 208 remains unchanged as the applied pressure 202 increases to the diastolic blood pressure (DBP). The optical reflectance plot 210 peaks at a point 210 when the applied pressure 202 is equal to the diastolic blood pressure. As the applied pressure 202 increases beyond the diastolic blood pressure, the optical reflectance plot 210 decreases as shown by section 210B since, as discussed above, the blood vessel 206 is compressing and, thus, the blood volume 208 within the detection range of the optical sensor 110 is decreasing in section 208B.

The optical reflectance plot 210 is a plot of optical reflectance peaks 211 of the reflectance signal 214 (FIG. 2A) detected by the optical sensor 110 (FIGS. 1A-1C) for a given heartbeat. When the applied pressure 202 is equal to the diastolic blood pressure, the detected optical reflectance peak 211 is greater than the detected peak 211 when the applied pressure 202 is less than the diastolic blood pressure. As discussed above, this phenomenon is due to the tissue 204 being compressed thereby allowing for a greater intensity of light to be detected at the optical sensor 110. As the applied pressure 202 increases beyond the diastolic pressure, the detected optical reflectance peaks 211 are shown as decreasing to a minimum.

Figure 3:
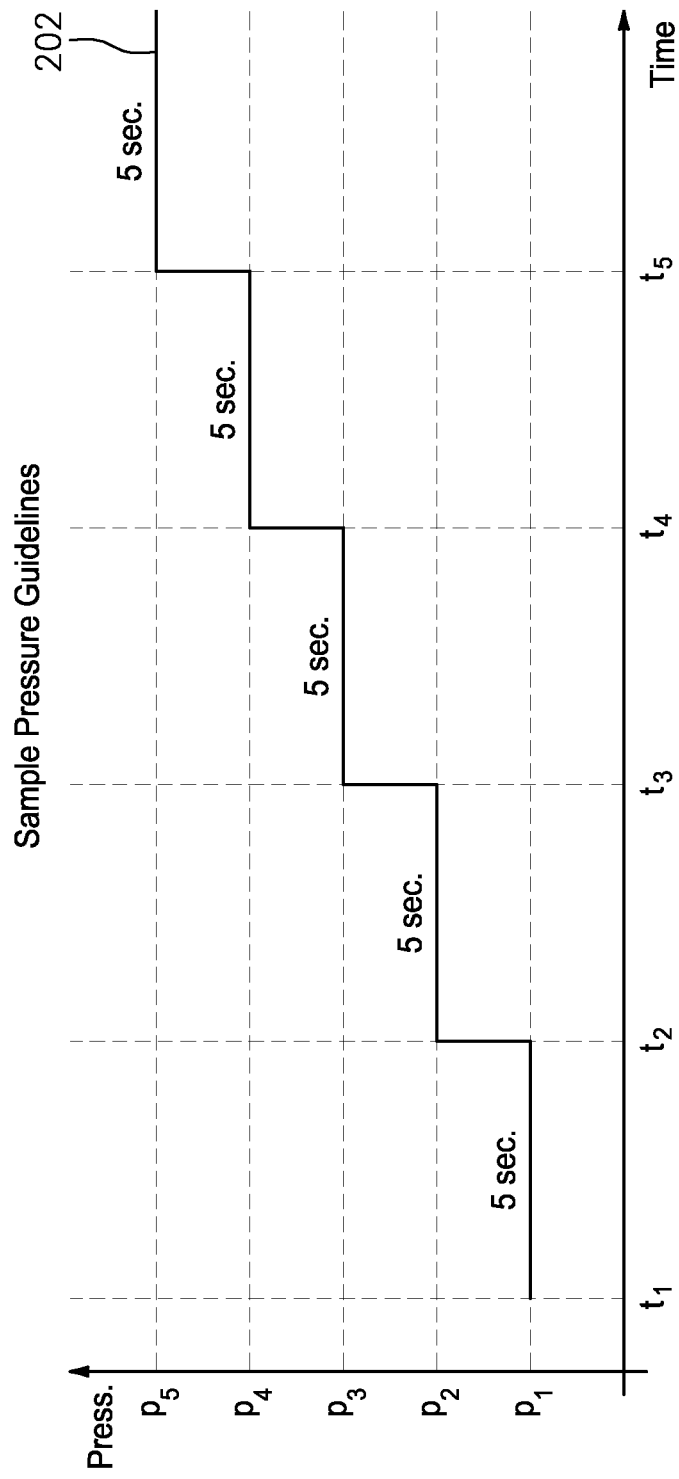
FIG. 3 shows a chart of applied pressure over time in accordance with embodiments of the present disclosure.

Referring to FIG. 3, instead of increasing the applied pressure 202 continuously, as discussed above, the applied pressure 202 may be increased step-wise. In the sample case shown in FIG. 3, the applied pressure is step-wise increased to five different applied pressure levels (or steps) $P_1$, $P_2$, $P_3$, $P_4$, $P_5$ at various times $t_1$, $t_2$, $t_3$, $t_4$, $t_5$ for five second durations. In the data plot of FIG. 4A, the applied pressure (AP) 202 was applied at seven (7) different force levels (or stages or steps) for a period of three seconds each taken at a 30 Hz sample rate.

Figure 4A:
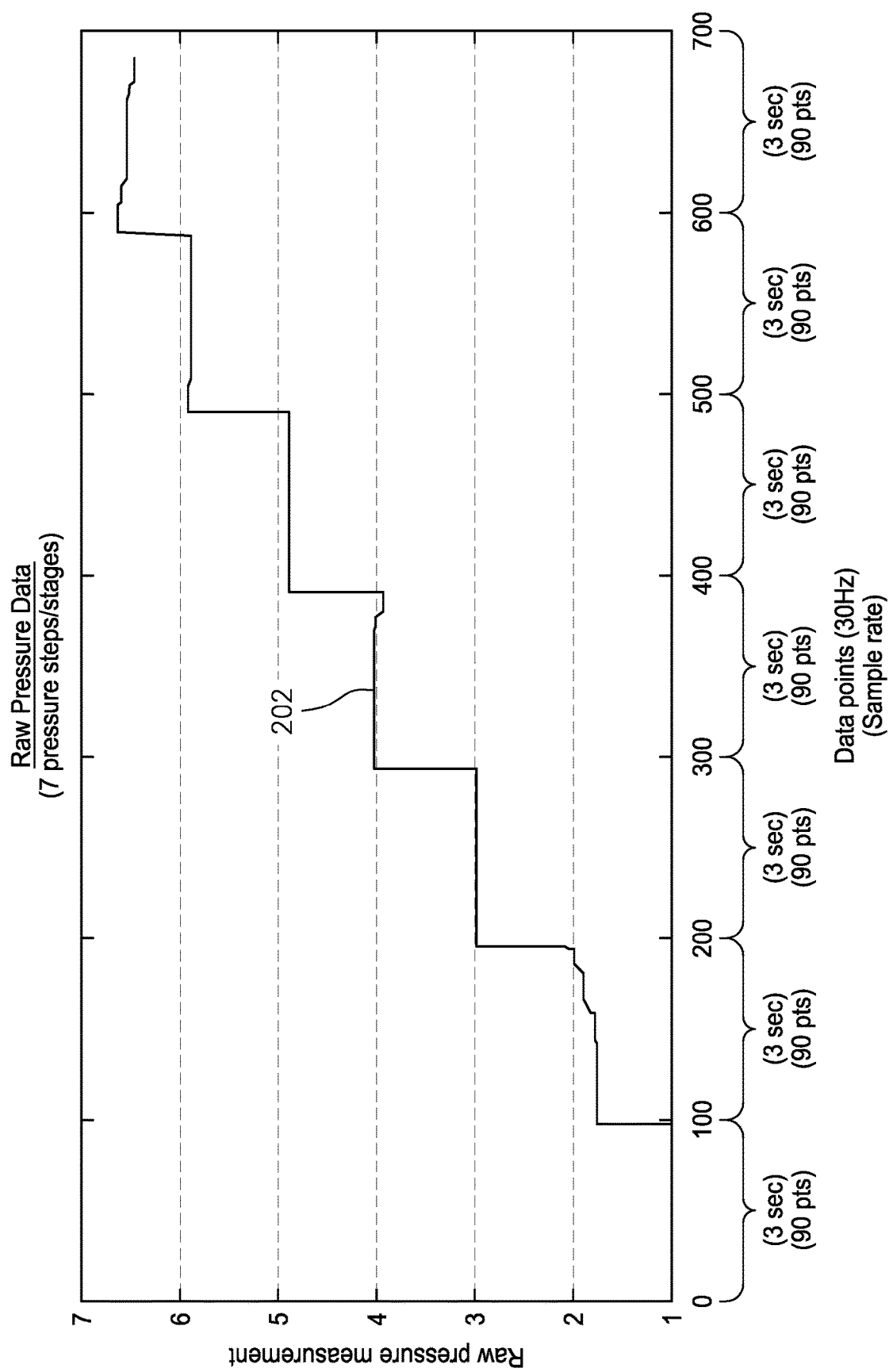
FIG. 4A is a sample plot of raw pressure measurement data measured over time in accordance with embodiments of the present disclosure.
Figure 4B:
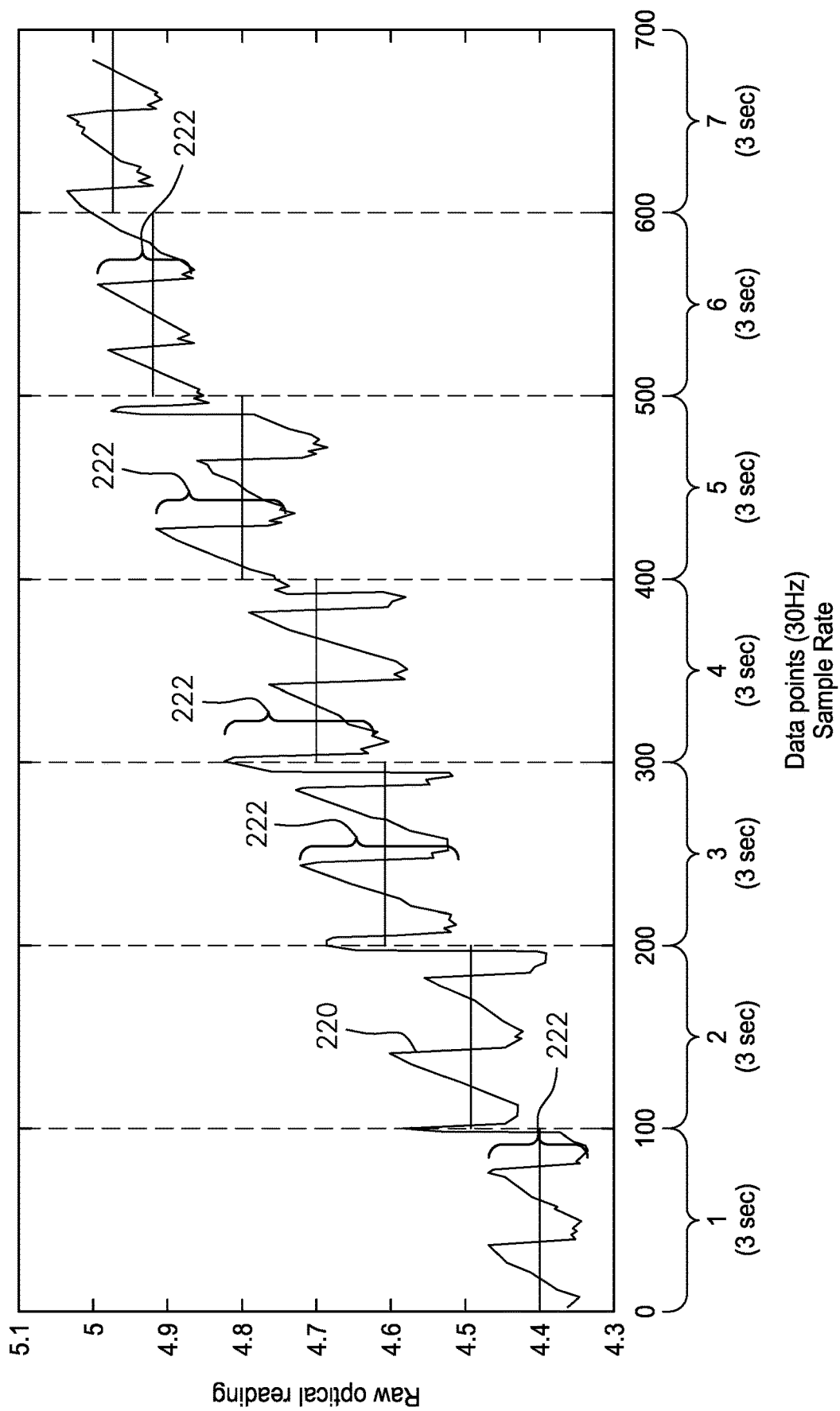
FIG. 4B is a sample plot of raw optical data collected by an optical sensor of a blood pressure measuring device during the pressure applied resulting in the plot of FIG. 4A in accordance with embodiments of the present disclosure.

Referring to FIG. 4B, sample raw optical data 220 is plotted at a data collection frequency of 30 Hz with the step-wise increasing applied pressure of FIG. 4A, which corresponds to 90 samples over a 3 second hold time. While the raw optical data 220 fluctuates, the average optical reflection (peak to peak) magnitude 222 may be recorded and plotted, and the optical reflectance plot 210 of the peaks may be determined, as discussed herein. The controller 112 (FIG. 1B) correlates the raw optical data 220 optical reflection magnitudes 222 and generates an optical reflectance plot 210 corresponding to the peak magnitudes 222.

Figure 4C:
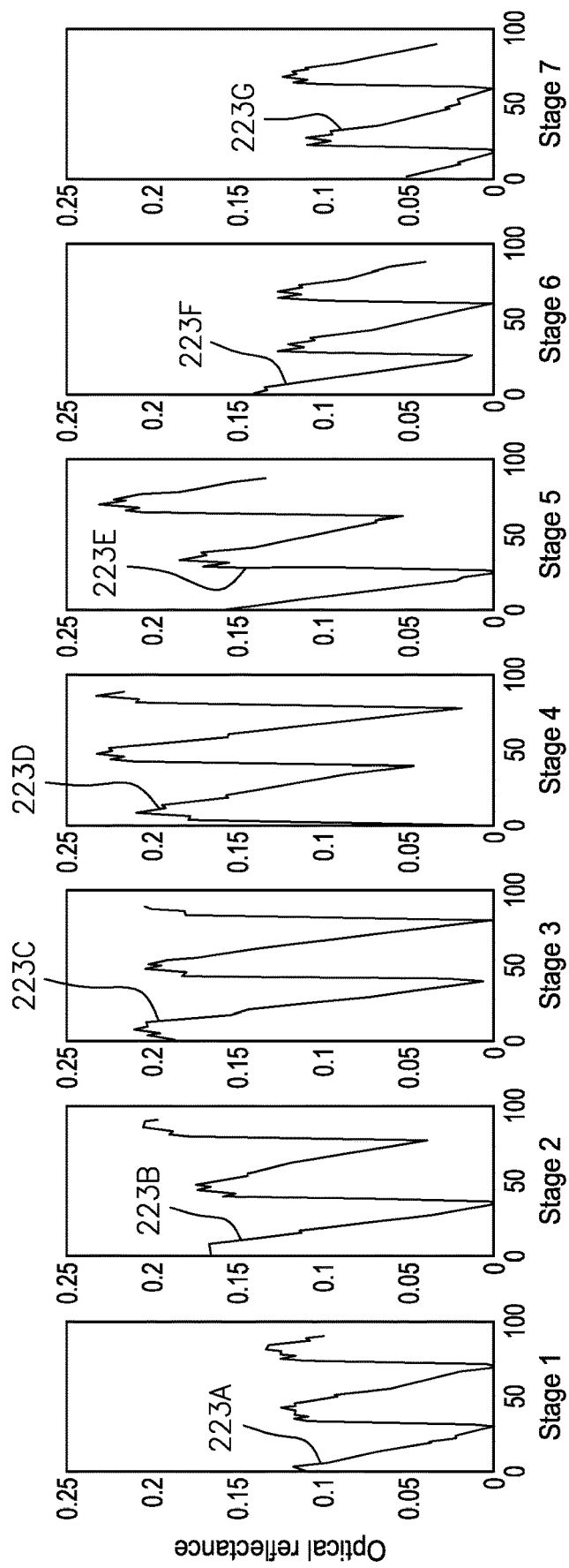
FIG. 4C is a sample side-by-side comparison plot of the raw optical data of FIG. 4B with the DC pressure component removed in accordance with embodiments of the present disclosure.

Referring to FIG. 4C, the controller 112 is configured to plot the raw optical data 220 such that peak amplitude over time is plotted with the DC pressure component removed. As shown in FIG. 4C the DC pressure component is removed from the optical intensity peak and the optical data plots from each pressure stage are presented in a side-by-side comparison for a period of two heartbeats. There are seven optical peak plots 223A-223G.

Figure 4D:
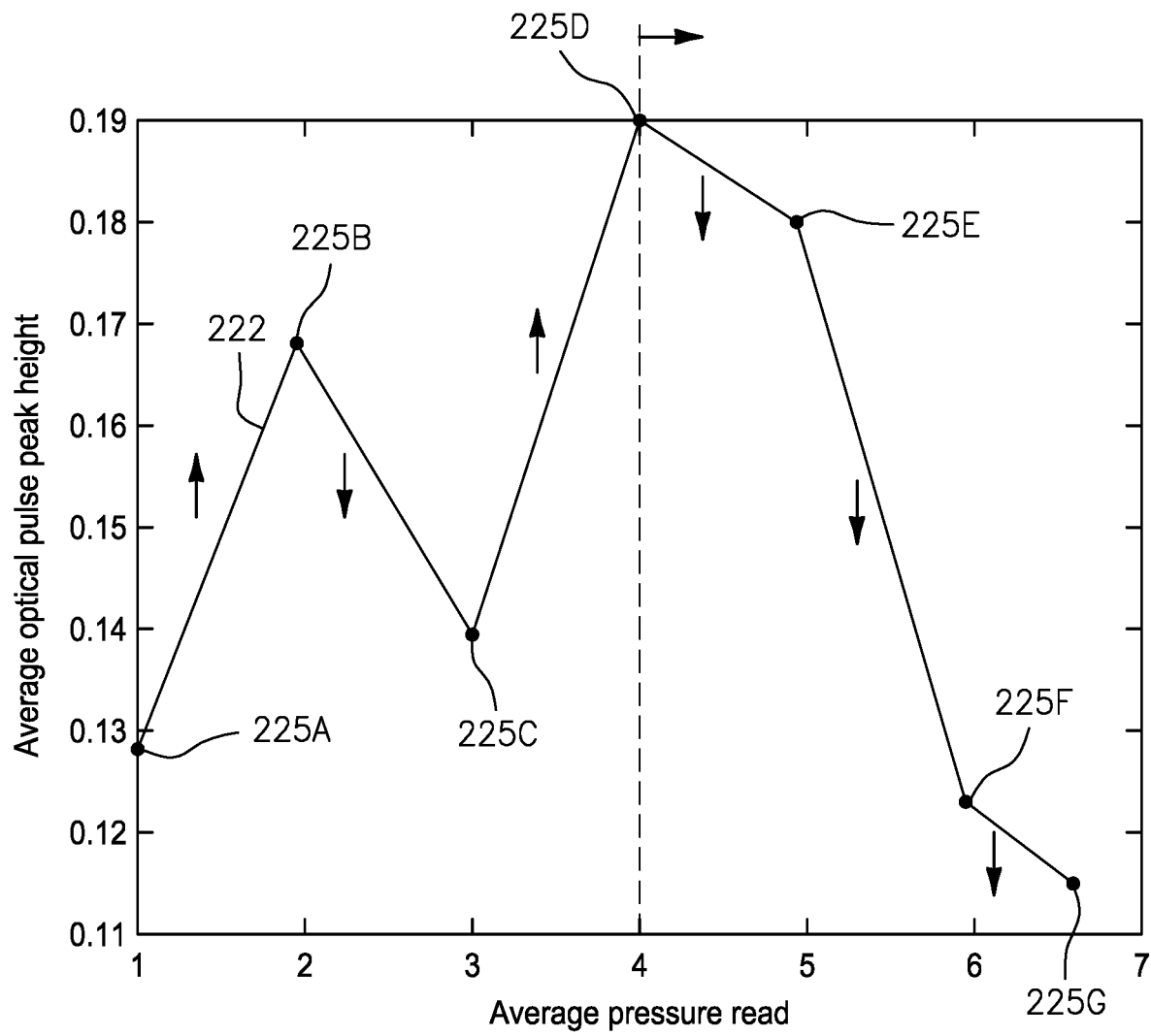
FIG. 4D is a sample plot of the average optical pulse peak heights of FIG. 4C in accordance with embodiments of the present disclosure.
Figure 4E:
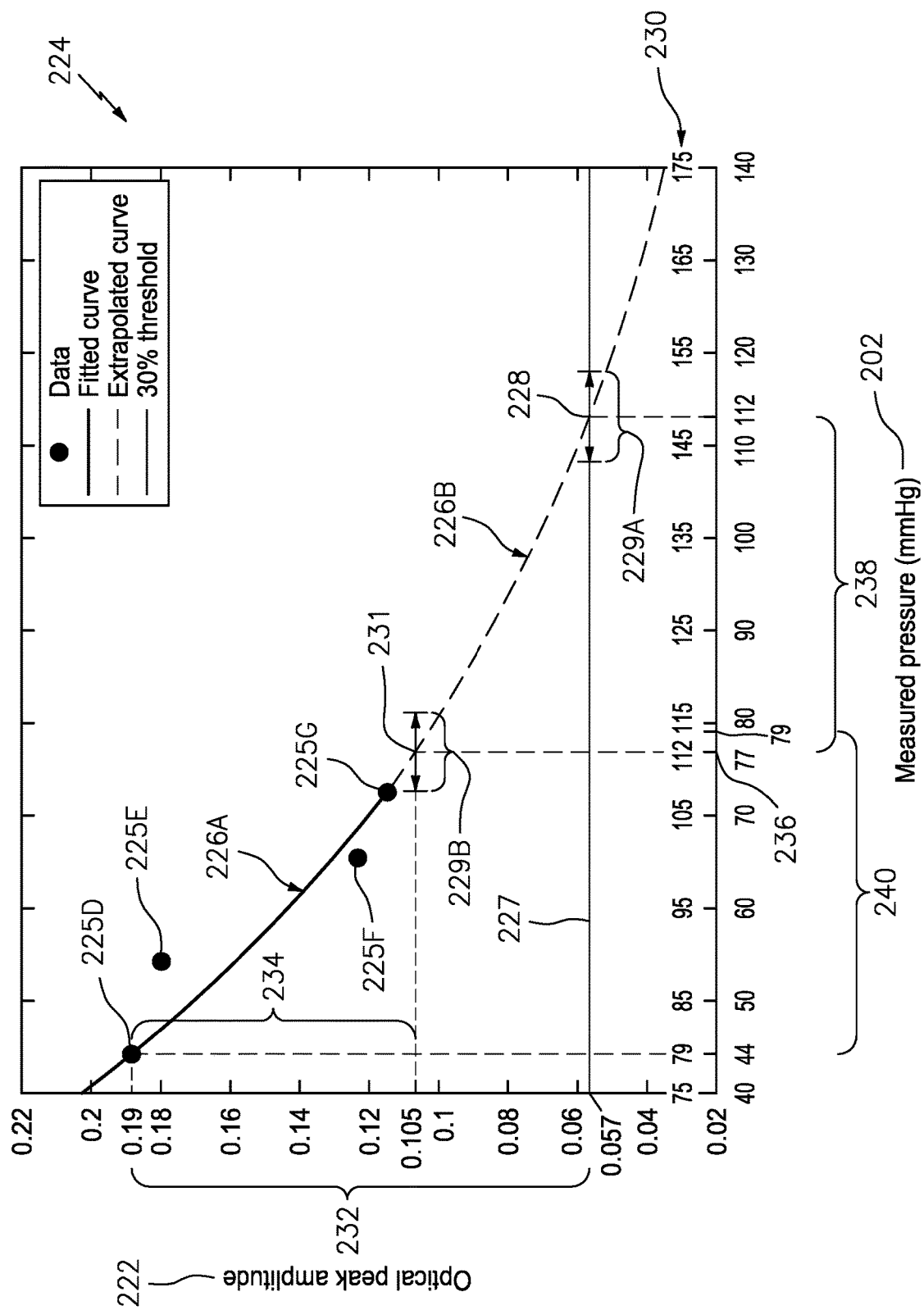
FIG. 4E is a sample plot of a portion of the optical pulse peak heights of FIG. 4D plotted against measured pressure during the pressure applied resulting in the plot in accordance with embodiments of the present disclosure.

Referring to FIG. 4D, the controller 112 is configured to plot the average optical pulse peak height over the average applied pressure measured (or read) by the pressure sensor 104 from averages of the optical peak plots 223A-223G. The averaged data points 225A-225G, corresponding to the averaged peak heights of optical peak plots 223A-223G, are plotted and the controller 112 is configured to determine the maximum peak before declining to a minimum using a standard peak finding algorithm. In the case shown in FIG. 4D, the maximum peak for the data set is shown at data point 225D (corresponding to optical peak plot 223D). Referring to FIG. 4E, the controller 112 is configured to plot the data points beginning at the maximum peak 225D before decline and onward. The controller 112 is configured to perform a curve fit (e.g., first order exponential fit) on the optical and pressure data measured and generate a fitted curve 226A of the determined optical reflection magnitude 222 as a function of measured pressure 202, such as shown by the below equation.

$$y=Ae^{Bx} \quad \text{Eq. 1}$$

In this case, "y" corresponds to the detected optical peak values and "x" corresponds to the measured pressure values (in mmHg). The values of A and B for the optical and pressure data points shown in FIG. 4E for a first order exponential fit curve shown in Eq. 1 are A=0.3955 and B=−0.0171. As the optical reflection peak magnitudes 222 decrease after the applied pressure is greater than the diastolic blood pressure of the user, data points 225D-225G are plotted and the fitted curve 226A to the data points 225D-225G is plotted as curve 226A. In some embodiments, the fitted curve 226A may be extrapolated to a point beyond the applied pressure 202 data collected to determine the desired correlation to blood pressure, such as the SBP value, by multiplying the optical value by an SBP Ratio value (e.g., 30% or 0.3), and determine the corresponding pressure value from Eq. 1. The extrapolation along the curve fit curve 226A of Eq. 1 may be plotted as an extrapolated curve 226B (dashed line). The extrapolation point used to determine the SBP value can be a predetermined point on the extrapolated curve 226B. For example, the controller 112 can use the fitted curve of Eq. 1 to extrapolate a point that is 30% of the maximum of the collected optical peak magnitude 225D. While the curve fit equation shown above is a first order exponential curve fit using non-linear least squares method, other curve fit equation types, orders, and/or methods are within the scope of the present disclosure, provided they provide the desired accuracy.

For embodiments where the pressure sensor has sufficient overall range to measure an applied force strong enough to collapse or substantially collapse the blood vessel being measured, extrapolation of the curve may not be needed to determine SBP and the value of SBP may be determined directly from the measured optical data and measured force sensor data indicating when the vessel has collapsed or substantially collapsed. In that case, there may be an offset for SBP value that may be determined during a calibration process, similar to that described for DBP offset. Also, in that case, the curve fit of the optical data would also not be needed or be optional as a calibration or quality checking feature.

The measured pressure values, "x", may be detected by the force sensor 104 (FIG. 1A) and transformed by the controller 112 (FIG. 1A) into any form of pressure units. For example, the controller 112 could convert the measure pressure values "x" from the device force reading to mm Hg by the following equation:

$$x=\text{Pres.}/0.0208333*9.8/0.32/133.322368 \quad \text{Eq. 2}$$

where Pres. is determined from a device force reading (in "force units") as follows: Pres.=weight/area; weight=mass*gravity; gravity=9.8 (unit m/s$^2$); mass (unit g)=device force reading (in force units)/0.0208333 (granularity of force sensor); fingertip area=3.2 cm$^2$; and 1 mm Hg=133.322368 Pa. The fingertip area may be a predetermined constant value using an average fingertip surface area or may be determined dynamically by the device through the force sensor. The above values correspond to use of an iPhone 6S® device made by Apple, Inc. The calculated pressure values may be used together with the corresponding measured optical peak values as x,y data points for performing the curve fit (e.g., to fit Eq. 1) described hereinabove. Other equations may be used based on the force sensor used.

In the case shown in FIG. 4E, the peak point 225D has an optical peak amplitude 222 of 0.19 at a measured pressure of about 44 mm Hg which is equal to the diastolic blood pressure (DBP), as discussed herein above with FIG. 2B (AP=DBP). The controller 112 then determines that the (uncalibrated) user diastolic blood pressure (DBP) is 44 mm Hg. The actual DBP of the user is then determined by applying an offset value (or DBP Offset), e.g., 35 in this case, to obtain the actual DBP of the user or 77 mm Hg (44+35), discussed more hereafter. For determining the user systolic blood pressure (SBP), the controller 112 extrapolates the fitted curve 226A by way of the extrapolation curve 226B to a predetermined point at 30% (SBP Ratio) of the peak optical value 0.19, or 0.057 (i.e., 0.19×0.3), and then calculates that the systolic blood pressure (SBP) of the user is equal to the theoretical applied measured pressure at an optical peak magnitude of 0.057. The predetermined extrapolation point 30% (may be referred to herein as SBP Ratio) may be based on calibration, user averages or a predetermined value or other approaches (discussed hereinafter). Values other than 30 may be used if desired, provided it provides the desired measurement accuracy. In this case, the 30% value shown as a horizontal line 227 at value 0.057 optical peak amplitude intersects the extrapolated curve 226B (using Eq. 1) at an extrapolated data point 228 that corresponds with a measured pressure (extrapolated) of 112 mm Hg. There may be a given margin of error 229A of the actual systolic blood pressure (SBP) by extrapolating the applied pressure point in this manner. The pressure units are shown in mm Hg, but other pressure units are within the scope of the present disclosure.

Based on the various different force levels applied by the user that are detected by the force sensor 104 (FIG. 1A) and the plurality of optical signals detected by the optical sensor 110 (FIG. 1B), the controller 112 (FIG. 1B) is configured to determine a periphery blood pressure value at the fingers of the user. The controller 112 determines that the diastolic blood pressure is equal to the peak of the optical reflectance plot 210 (discussed hereinafter) generated based on optical data received from the optical sensor 110 with an optional offset value that may be determined based on calibration of the blood pressure measurement device 10 for a given user. For example, the offset value may be calibrated with contemporaneous comparisons to empirically collected data of a user(s) with a different blood pressure measurement device(s). For example, in the case shown in FIG. 4E, the optical reflectance plot maximum peak at point 225D corresponds to a value of measured pressure value of 44 mm Hg, but if a predetermined offset value of "35" is obtained through calibration for the blood pressure measurement device 10 used, then the blood pressure measurement device 10 would store the user's diastolic blood pressure as 79 mm Hg (44 mm Hg+35 DBP offset value). The DBP offset value is shown in FIG. 4E as the spacing 240 along the x-axis. Once the DBP and SBP are known, the controller 112 provides the blood pressure values to the user (SBP/DBP), in this case 112/79.

In some embodiments, an offset value may be used for determining the systolic blood pressure (SBP) similar to as described above for determining the diastolic blood pressure (DBP). The net effect of using an offset value for determining the systolic blood pressure would be to shift the fitted curve 226A and/or the extrapolated curve 226B shown in FIG. 4E to the right or left by the offset value. In FIG. 4E, the shifted curve x-axis 230 is shown for an offset value (such as the DBP Offset) of "35." As such, the predetermined extrapolation point (SBP Ratio) may be different if an offset value is used. For example, if an offset value is used shifting the fitted curve 226A and extrapolated curve 226B to the right, then instead of using 30% (or 0.33) of the optical peak 225D as a predetermined extrapolation point along the curve fit equation (Eq. 1) to obtain the SBP value, an optical value corresponding to the shifted curve (e.g., 55% or 0.55) (or others) of the optical peak 225D could be used to determine the extrapolated data point (as may be determined from device calibration discussed hereinafter). In that case, the value of SBP would be determined by adding the offset (in this case 35) to the pressure value obtained from the curve fit. As shown in FIG. 4E, if using an offset value, the extrapolated point 231 can be closer to the fitted curve 226A, which may lead to a reduction in the error margin 229B. Using an offset value in this manner may reduce the potential for error when extrapolating or estimating the extrapolated data point 231 since the shape/slope of the extrapolated curve 226B can affect the error margin 229A, 229B when extrapolating the data point 228, 231 where the systolic blood pressure is projected to be for the user.

Below are example equations that can be used by the controller 112 to determine diastolic blood pressure (DBP) while using a pressure DBP Offset of 35 mmHg, and to determine systolic blood pressure (SBP) without using an offset, but relying on a predetermined point along the curve fit, in this case using a y value adjusted by a SBP ratio value of, e.g., 30% (or 0.30), which may be determined during a calibration procedure described herein.

$$DBP(x)=\ln(y/A)/B+35=\text{Measured DBP}+35 \quad \text{Eq. 3}$$

$$SBP(x)=\ln(y*0.3/A)/B \quad \text{Eq. 4}$$

Where "y" is the measured optical value and SBP (the "x" value) is the output pressure value (SBP) from the optical curve fit (OCF), e.g., Eq. 1. Also, DBP may be determined directly from the measured pressure value (Measured DBP) in mmHg (as converted from the force sensor 104, as described herein), as is also shown in Eq. 3, and corresponding to the peak optical signal as described herein. In some embodiments, DBP may be determined by plugging the peak optical signal value ("y") into the left side of Eq. 3 and calculating DBP. Other DBP Offset and SBP Ratios values are within the scope of the present disclosure and may be used if desired, provided they provide the function and/or performance described herein.

A sample calibration process for calibrating the blood pressure measurement device 10 may be as follows. First, measure the "actual" user blood pressure values: Actual SBP and Actual DBP, e.g., 120/80 (Actual SBP/Actual DBP) from an independent blood pressure measurement device, e.g., using a blood pressure cuff technique. Then, put the software application running on the blood pressure measurement device 10 in "calibration mode" and run the software application to collect the optical data points at a plurality of stages, e.g., at seven pressure stages. Then, perform an exponential curve fit of the decreasing optical data, e.g., using an Optical Curve Fit ("OCF") equation or $y=Ae^{Bx}$, where "y" is the optical signal and "x" is pressure, to determine the OCF equation fit coefficients A, B. Then, determine the DBP pressure (DBP Curve Fit) from the OCF equation curve for the first optical point (DBP Optical) where the optical curve peaks. Then, calculate DBP offset value from the measured actual DBP by the following equation.

$$\text{DBP Offset} = \text{DBP Actual} - \text{DBP Curve Fit} \qquad \text{Eq. 5}$$

Then, calculate SBP Optical value from the measured Actual SBP by plugging in the Actual SBP into the OCF equation (with or without a curve shifting offset value such as the DBP offset value discussed above). Then, calculate an SBP Ratio value in accordance with the following equation.

$$\text{SBP Ratio} = (\text{SBP Optical}) / (\text{DBP Optical}) \qquad \text{Eq. 6}$$

In this case, if the Actual SBP for the user is 112 mmHg, the value of the corresponding optical peak value would be 0.057 and thus the SBP Ratio (shown by the spacing 232) would be 0.057/0.19 (SBP Optical)/(DBP Optical)=0.3 (or 30%), as discussed hereinabove.

Once the values of DBP Offset and SBP Ratio are determined, the calibrated values of DBP Offset and SBP Ratio for use by the BP software application (or BP App, as discussed herein) running on the blood pressure measurement device 10 for determining the extrapolated data point where SBP of the user is projected to be located.

In some embodiments, if calibrating using the shifted curve (x-axis upper scale 230 in FIG. 4E), the SBP ratio may be greater than the SBP ratio calculated with the unshifted curve. In particular, if the actual SBP is 112, the shifted OCF value would be at a point 236, corresponding to the pressure value (x) of 112 mmHg on the shifted x axis scale 230 or a shifted value of 77 mmHg (SBP actual−DBP offset or 112−35=77), shown as a shift 238, and the corresponding optical value (y) from the OCF curve 226A at point 231 would be approx. 0.105. In that case, the value of the corresponding optical peak value would be 0.105 and thus the SBP Ratio using the shifted curve (shown by the spacing 234) would be 0.105/0.19 (SBP Optical)/(DBP Optical)=0.55 (or 55%).

As discussed hereinabove, in some embodiments, the use of a shifted curve to calculate the pressure may reduce errors associated with curve fit errors, because the value for the SBP Ratio is determined closer to the measured optical data points. For example, a given error in the curve fit, e.g., due to general curve fit error or optical data point measurement error or other error, may introduce a larger error band 229A at the point 228 (using an unshifted curve) than the corresponding error band 229B at point 231 (using a shifted curve), which may cause the value for calculated SBP Ratio during calibration to have a lower tolerance for errors if an unshifted curve is used. This would need to be compared to any error introduced by using the same offset for DBP as for SBP to see which approach introduces the least amount of error.

The above-described calibration technique may be performed by the user alone or may be performed by the user and one or more medical professionals. For example, the user may go to a doctor's office in order to use an independent blood pressure measurement device to obtain the necessary blood pressure data of the user (DBP, SBP) discussed above for calibrating the blood pressure measurement device 10, which may be converted to digital data (e.g., digital blood pressure data) and may be stored on a server (or other digital storage device) which is accessible by the device 10 and/or transmitted to the device 10 or to a server that communicates with the device 10, e.g., over a network, such as is described herein with FIG. 10. The digital calibration data (e.g., DBP offset and SBP Ratio) from a plurality of users may be aggregated, stored and analyzed by a computer system which may be accessible by the BP App on the device 10 for informing and/or updating certain predetermined values or other calibration coefficients of the BP App. For example, calibration data could be aggregated by digital tags or labels associated with qualities, attributes or characteristics of the user(s), such as, without limitation, height, age and weight, or other user factors, attributes or characteristics. Accordingly, a computer system or database may use the aggregated calibration data to adjust predetermined values or other calibration coefficients used in blood pressure measurement devices 10 or BP App that are not calibrated to the specific user using that device 10. For example, a database may collect values for a DBP Offset and SBP Ratio for various demographic groups based on age, height, BMI, or other characteristics, and determine average values that can be used by the BP measuring software application (BP App) to determine the best initial values for the user. Advantageously, these values can be used without the need for the user to calibrate the device.

In addition, the present disclosure may learn and/or optimize the values of the BP measurement calculation (or algorithms, coefficients, and the like) over time using analytics, "big data", real-time global data networking, artificial intelligence and machine learning techniques to continuously learn over time to optimize the BP calculation for a given user or a group or "class" of users based on a user factors, attributes, characteristics, e.g., certain demographic groups, such users within a certain range of weight, age, BP, or the like. In that case, the controller (or logic contained therein) may "train" (or "learn") using data belonging to a given "class" of users to optimize the BP calculation for that group. The logic of the present disclosure may use such techniques to obtain the latest BP calculations and correlate them to user (or patient) data to optimize BP measurement calculations or provide more personalized and accurate BP calculations for a user, continuously in real-time, and which adjusts, learns, optimizes and improves continuously in real-time the BP measurement calculations for the current user (or patient) and other users (or patients). Such learning or optimization may be done by known machine learning, artificial intelligence, expert systems, predictive analytics/modeling, pattern recognition, mathematical optimization, deep learning algorithms, neural networks, support vector machines (SVMs), decision tree classifiers, logistic regression, random forest, or any other techniques and technology that enable the accuracy of the BP calculations to improve over time. The system of the present disclosure may also receive feedback from users of other BP measurements received, e.g., at a doctor's office or otherwise, and use that data to train the logic to identify what calculation parameters work best for users with certain input characteristics.

In some embodiments, the blood pressure calculations, algorithms, coefficients, and/or fitted curves, as well as the number of pressure levels, pressure tolerances, and hold times may be determined and/or optimized for each user or group or class of users using the above techniques.

In some embodiments, blood pressure measuring devices and methods may obtain a blood pressure measurement (or reading) without the use of an optical sensor. In devices without an optical sensor, the user may perform the pinching process as described above, and the force sensor 104 (FIG. 1A) will collect the applied pressure 202 and pressure oscillation 216 data and transmit to the controller 112 (FIG. 1B) as described above. Thus, the blood pressure determination will be made based on the applied pressure 202 data and pressure oscillation 216 data without a correlation with optical reflectance data. The controller 112 determines that the diastolic blood pressure is equal to the applied pressure 202 at the point where the pressure oscillation 216 data begins to increase. The controller 112 determines that the mean blood pressure is equal to the peak of the pressure oscillation 216 data. In such embodiments, it is not necessary to have an activated light source since there is no optical data being collected.

In embodiments where a blood pressure determination is made using a force sensor 104 and an optical sensor 110, the controller 112 can correlate the determined blood pressure values for accuracy. Thus, for correlation of the diastolic blood pressure determination, the controller 112 can correlate whether the applied pressure 202 at the point where the optical reflectance 210 curve peaked is substantially the same as the applied pressure 202 where the pressure oscillation 216 curve began to increase. If the correlation is within a predetermined tolerance range, then the controller 112 can select one of the applied pressure 202 readings as corresponding to the diastolic blood pressure or average the applied pressure 202 readings as corresponding to the diastolic blood pressure. If the correlation is not within a predetermined tolerance range, then the controller 112 may be configured to instruct for the pinching process to be repeated and/or instruct for calibration of the force sensor 104 and/or optical sensor 110.

Figure 5A:
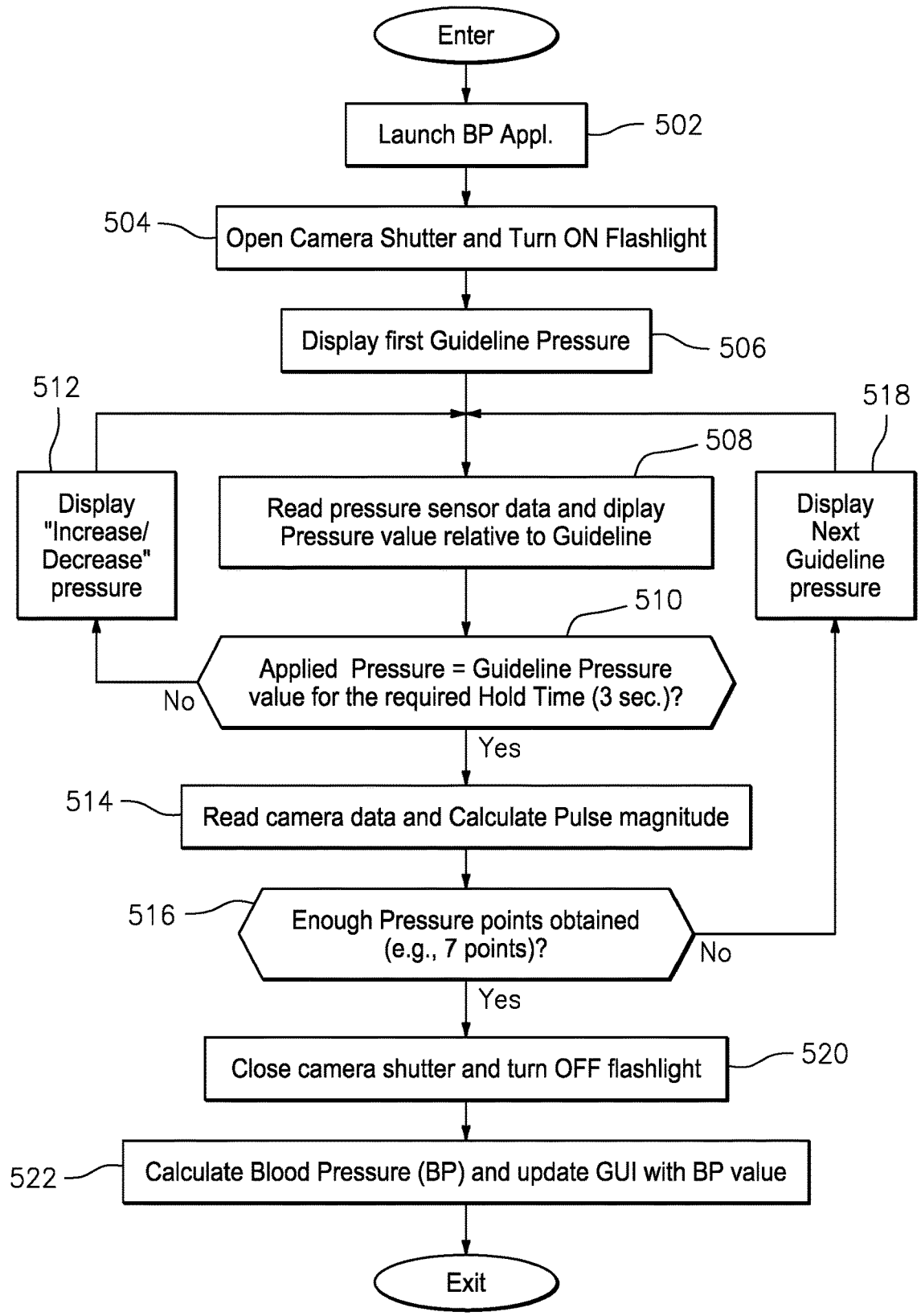
FIG. 5A is a flow diagram of a blood pressure measuring method being performed on a blood pressure measuring device in accordance with embodiments of the present disclosure.

Referring to FIG. 5A, a method flow diagram 500 of a blood pressure measuring method being performed on a smart phone is shown. The method 500 begins at block 502, where a blood pressure measurement software application is launched on the device. Then at block 504, an instruction is sent to open a camera shutter on the device and to turn on the device's light source. Then at block 506, a display screen of the device e displays a first guideline pressure value. Then at block 508, a force sensor (or pressure sensor) of the device reads pressure sensor data being applied to the device and displays pressure value relative to the displayed first guideline. Then at block 510, the device determines whether the applied pressure/force is equal to the first guideline pressure/force within an upper and lower tolerance, e.g., +/−X force units (or pressure in PSI or mmHg as per Eq. 2 herein, or other pressure units) of first guideline pressure/force.

If the detected pressure is not within the tolerance of the first guideline pressure value, then the method 500 proceeds to block 512 and displays an "increase pressure" notification if the detected pressure is less than the first guideline pressure and allotted lower tolerance or displays a "decrease pressure" notification if the detected pressure is greater than the first guidelines pressure and allotted upper tolerance. In some embodiments, the display screen may change color or provide vibration feedback to the user when the detected pressure is outside the guideline pressure range (or tolerance). Then the method 500 returns to block 508.

If the detected pressure at block 510 is within the upper and lower tolerance of the first guideline pressure, then the method 500 proceeds to block 514 and detects optical sensor data (or camera data) and calculates pulse magnitude. Then at block 516, the device determines whether enough data points were collected at enough guideline pressures, e.g., seven (7) data points of seven (7) different applied pressures at seven different guideline pressures. Other number of pressure levels or steps may be used if desired provided there are enough steps to calculate the blood pressure with the desired accuracy.

If the determined number of data points at block 516 is less than a predetermined number of data points, the method 500 proceeds to block 518 and displays the next guideline pressure value on the display screen of the device. The method 500 is then repeated for blocks 508-516 with the exception that the next guideline pressure value is used instead of the first guideline pressure value.

If the determined number of data points at block 516 is greater than or equal to a predetermined number of data points, the method 500 proceeds to block 520 and an instruction is sent to close the camera shutter and turn off the device's flashlight. Then at block 522, the device calculates blood pressure and updates the graphical user interface ("GUI") with a blood pressure value (discussed hereinafter).

While the notifications discussed above are described as being as visual notifications on the display screen of the phone, it is within the scope of the present disclosure for the notifications to be audio or haptic notifications, or for the notifications to be some combination of audio, visual and/or haptic notifications. Also, the pressure (or force) applied (or provided or exerted) by the user may in the form of pressure levels or steps or stages, or may be a continuously increasing or decreasing applied pressure (or force). When pressure steps are used, the device 10 may be able to obtain more samples at each pressure point (as compared to a continuously changing input pressure (or force)), which may provide a more stable or more accurate BP reading in some embodiments.

Figure 5B:
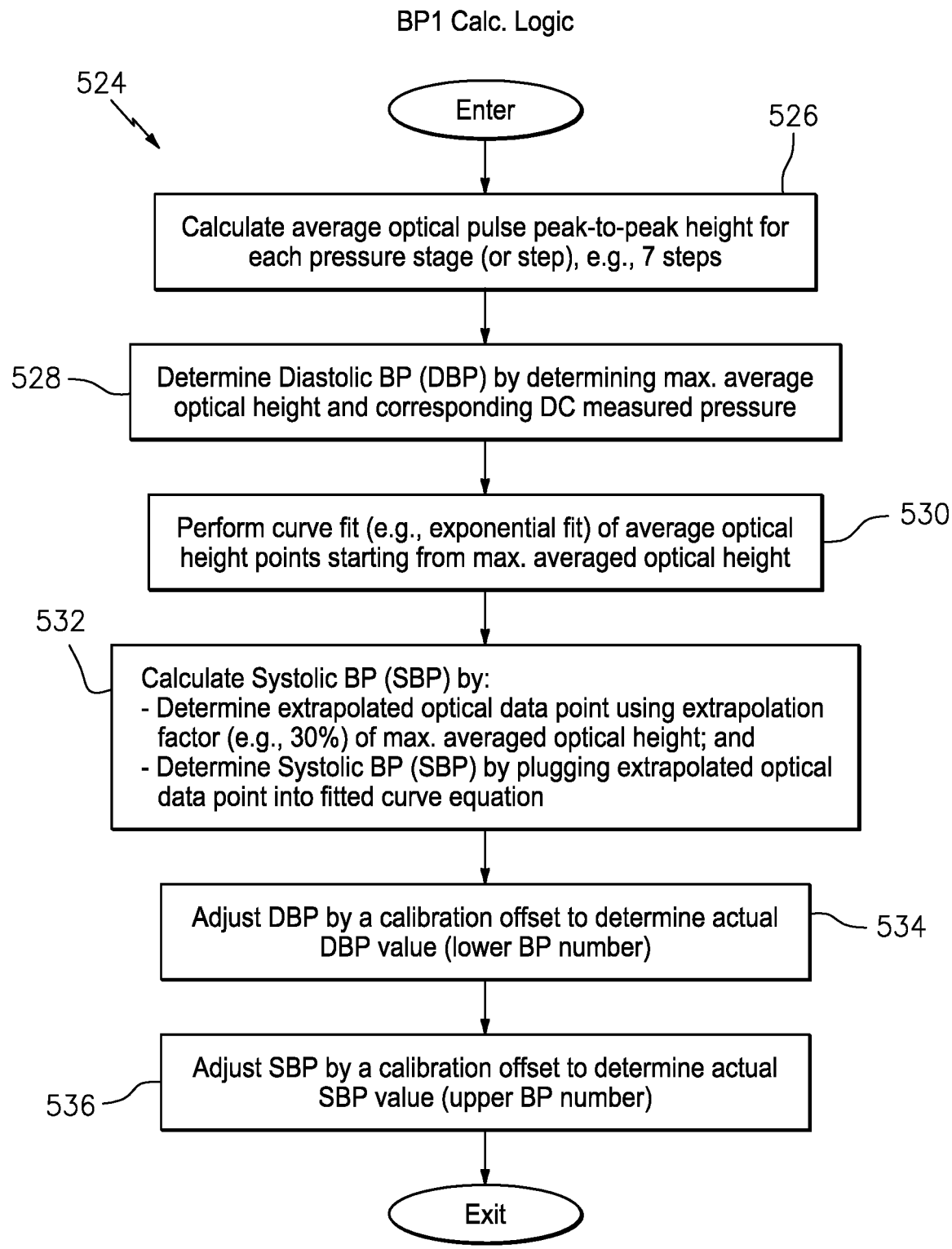
FIG. 5B is a flow diagram of a portion of the blood pressure measuring method of FIG. 5A in accordance with embodiments of the present disclosure.

Referring to FIG. 5B, an exemplary method flow diagram 524 is shown for performing the calculation of blood pressure at block 522 (FIG. 5A). The process 524 begins at block 526 with the device calculating an average optical pulse peak-to-peak height for each pressure stage (or step), such as that shown in FIGS. 4B and 4C. For example, an average optical pulse peak-to-peak height can be calculated for seven (7) pressure stages, but other amounts of pressure stages are within the scope of the present disclosure. Then at block 528, the device determines an initial diastolic blood pressure (DBP) value by determining a maximum average optical height and corresponding DC measured pressure. Then at block 530, the device performs a curve fit function (e.g., exponential fit) of average optical height points starting from the maximum averaged optical height. Then at block 532, the device calculates an initial systolic blood pressure (SBP) value by determining an extrapolated optical data point using an extrapolation factor of the maximum averaged optical height determined at block 528. The extrapolation factor (or ratio) can be any predetermined factor. For example, the extrapolation factor can be 30% of the maximum averaged optical height (other factor values may be used if desired). The systolic blood pressure (SBP) is determined by plugging the extrapolated optical data point into the fitted curve equation (OCF), Eq. 1, described herein. Then at block 534, the device adjusts (as needed) the determined diastolic blood pressure (DBP) by a calibration adjustment or offset to determine actual diastolic blood pressure (DBP or lower or bottom BP number) value, such as is described herein. Then at block 536, the device adjusts (as needed) the determined systolic blood pressure (SBP or upper or top BP number) by a calibration adjustment or offset to determine actual systolic blood pressure (SBP). Then the process 524 exits. The calibration adjustments for DBP and SBP in the steps 534, 536 may be any type of respective adjustment(s) or equation(s) specific for that parameter (DBP, SBP) that provides the desired calibration results for the respective parameter (DBP, SBP). The calibration steps 534, 536 may be performed in another portion of the process if desired, provided it provides the desired results or accuracy.

Figure 6A:
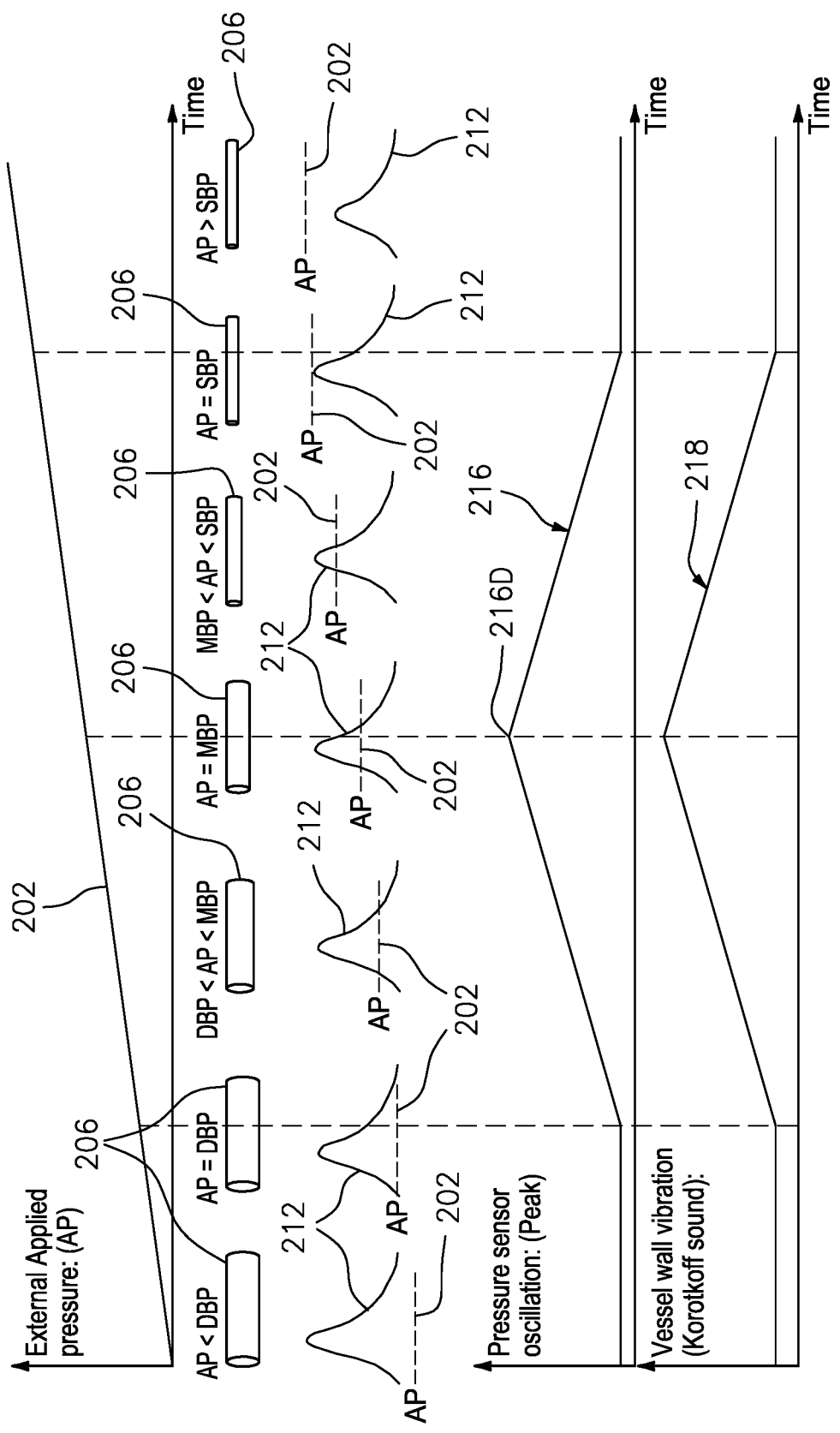
FIG. 6A illustrates blood vessel of a finger of a user at various stages of compression with accompanying pressure oscillation plot and blood vessel wall vibration plot in accordance with embodiments of the present disclosure.

Referring to FIG. 6A, the force sensor 104 (FIG. 1A) may be configured to detect pulse waves 212 generated by the user's heartbeats while the applied pressure 202 is being applied during the pinching process. The force sensor 104 (FIG. 1A) can detect slight oscillations (which may be referred to as "AC pressure" signal) caused by the swell of the blood vessel 206 as the pulse wave 212 moves through the point of compression within the detection range of the force sensor 104. The force sensor 104 may be configured to detect the pressure oscillations and transmit the pulse wave data to the controller 112 (FIG. 1B). The applied pressure 202 plot from FIG. 2B is shown with the decreasing tissue 204 and blood vessel 206 diagram series from FIG. 2B and also with a pulse wave 212 diagram series graphed in relation to the corresponding level of applied pressure 202. A pressure oscillation plot 216 of the peak detected pulse waves 212 is plotted with respect to applied pressure 202 based on pressure oscillation values detected by the force sensor 104 (FIG. 1A). As the applied pressure 202 increases, the force sensor 104 (FIG. 1A) detects a pressure oscillation plot 216 maximum of the pulse waves 212 when the applied pressure 202 is equal to the mean blood pressure (MBP) at a point 216D. The blood vessel 206 wall vibration plot 218 also exhibits a maximum when the applied pressure 202 is equal to the mean blood pressure, which may be referred to as the known "Korotkoff sound."

Figure 6B:
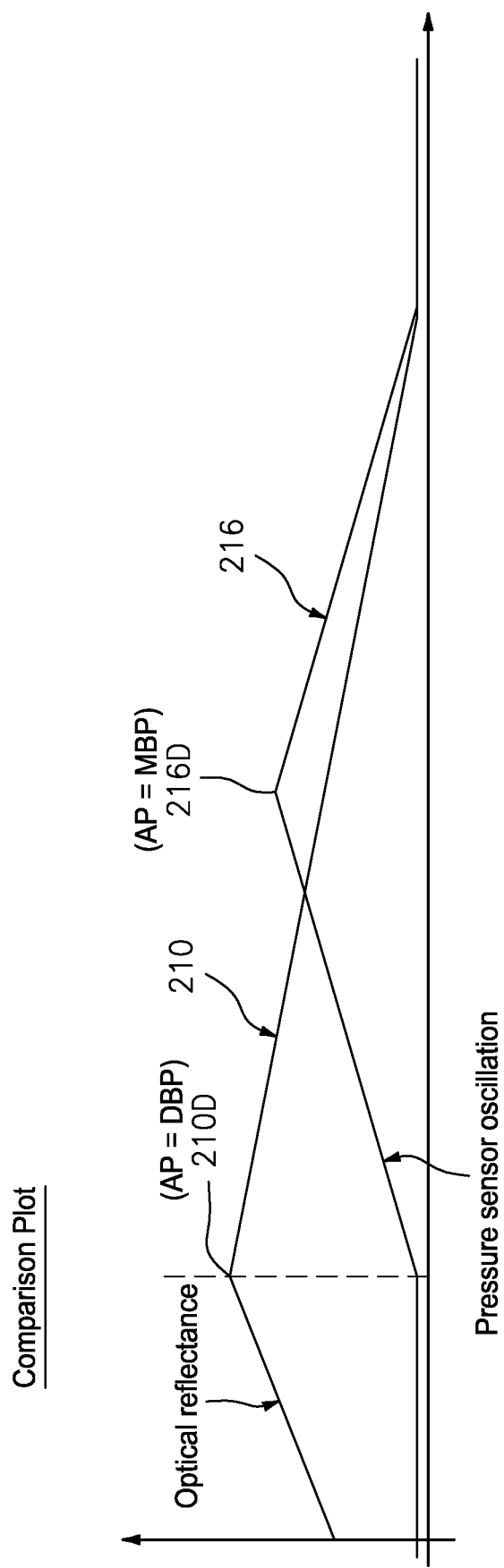
FIG. 6B illustrates an optical reflectance plot and oscillation peak plot with increasing applied pressure of a blood pressure measuring device in accordance with embodiments of the present disclosure.

Referring to FIG. 6B, the optical reflectance 210 shown in FIG. 2B is illustrated with the pressure oscillation plot 216 of FIG. 6A of the finger at the force sensor 104 (FIG. 1A). As shown in FIG. 6B, we have found that the peak 210D of the optical reflectance 210 of the finger at the optical sensor 110 (FIG. 1B) occur at different points in time as applied pressure increases from the peak 216D of the pressure oscillation plot 216 of the finger at the force sensor 104 (FIG. 1A). In particular, the optical signal peaks at 210D when the vessel blood pressure is at DBP (diastolic blood pressure), and the pressure oscillations peak at 216D, when the vessel blood pressure is at MBP (mean blood pressure). The units on the vertical axis are relative for this illustration.

Figure 6C:
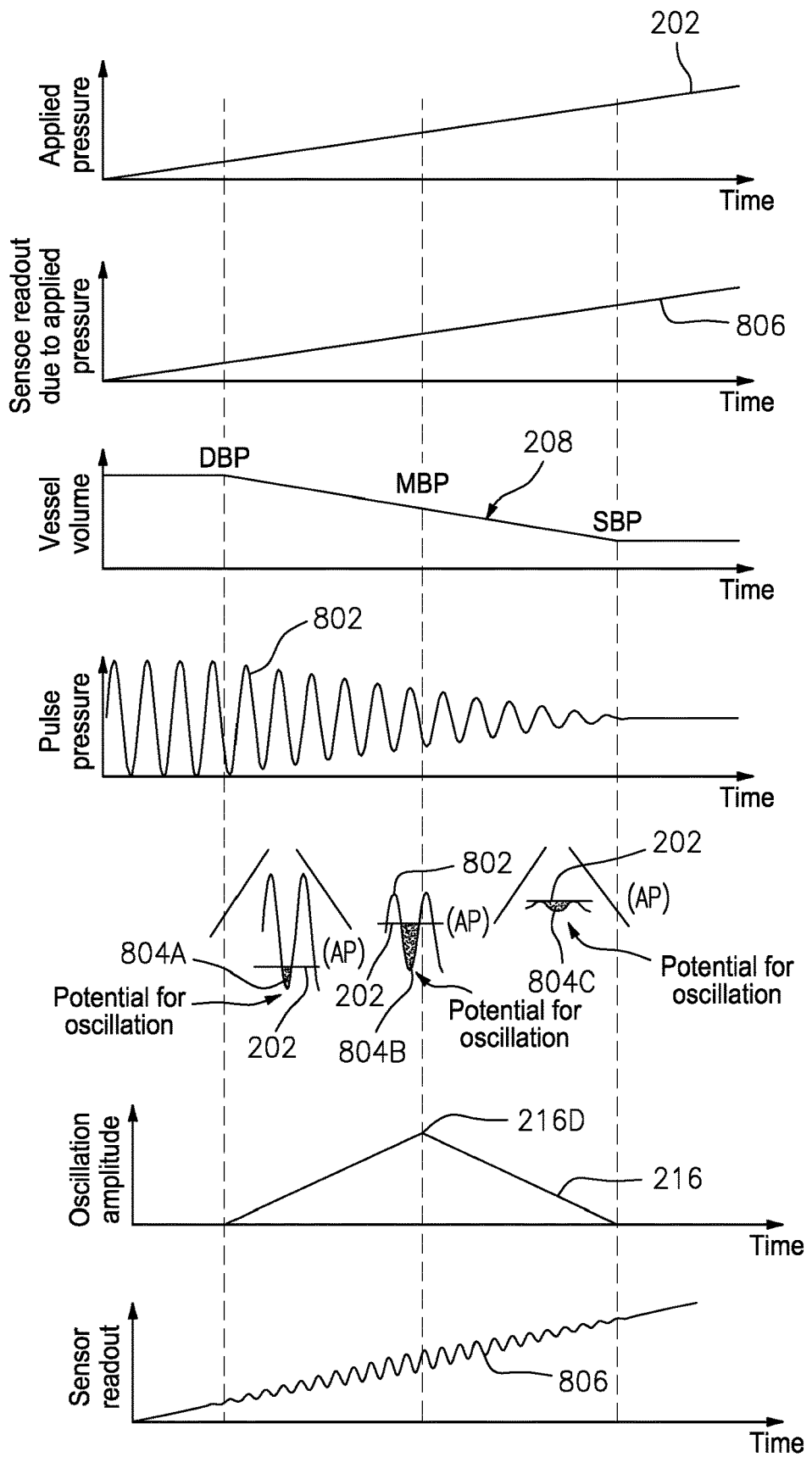
FIG. 6C is an illustration of a force sensor readout plot in comparison to increasing applied pressure with pulse pressure waveform shown in accordance with embodiments of the present disclosure.

Referring to FIG. 6C, illustrations are provided for illustrative purposes, and show why the pressure data collected by the device 10 (e.g., through the force sensor 104) may be correlated to a user's diastolic blood pressure (DBP), mean blood pressure (MBP) and/or systolic blood pressure (SBP) as described herein. The pressure oscillation amplitude (or peak) plot 216 exhibits a maximum at the mean blood pressure (MBP) of the user because oscillations are detected by the force sensor 104 (FIG. 1A) at times when the blood pressure in the blood vessel is below the applied pressure 202 but above the diastolic blood pressure (DBP). In particular, when the applied pressure 202 is equal to or below the blood pressure in the blood vessel (i.e., AP<=DBP, where DBP is the resting or lowest BP in the vessel) there is no detected oscillation in detected force values at the force sensor 104. The pressure oscillation is detected by the force sensor 104 when the applied pressure (AP) 202 is greater than the blood pressure in the vessel (i.e., AP>DBP), which is caused by the blood vessel wall collapsing under the force of the applied pressure 202. The potential for oscillation is greatest when the applied pressure is at the mean blood pressure (MBP) because: (i) in a decreasing direction of applied pressure 202 below the MBP, there are less moments in time (during a pressure pulse) when the blood pressure in the vessel will be less than the applied pressure 202, and (ii) in an increasing direction of applied pressure 202 above the MBP, the blood vessel will be in an increasing collapsed state from the applied pressure 202 where there is less compressibility (or play or deflection), or increased resistance to further compression, in the blood vessel wall for the blood vessel to collapse in order to provide a pressure oscillation that could be detected by the force sensor 104.

In particular, in the illustration example of FIG. 6C, the force sensor reading 806 is equal to the applied pressure (AP) 202 (i.e., the static or DC applied pressure) plus the AC pressure oscillation 804A, 804B, 804C. The oscillation 804A measured by the force sensor 104 corresponds to an example portion of the pulse pressure (PP) 802 curve when the applied pressure 202 is above but near the diastolic blood pressure (DBP). The oscillation 804B corresponds to an example portion of the pulse pressure 802 curve when the applied pressure 202 is substantially near the mean blood pressure (MBP). The oscillation 804C corresponds to a portion of the pulse pressure 802 curve when the DC applied pressure 202 is below but near the systolic blood pressure (SBP). The oscillation 804A, 804B, 804C is zero when the applied pressure 202 is less than the pulse pressure 802. The oscillation 804A, 804B, 804C is equal to the applied pressure (AP) 202 minus the pulse pressure 802 when the applied pressure 202 is greater than the pulse pressure 802. When the applied pressure (AP) 202 is greater than the diastolic blood pressure (DBP), the pulse pressure 802 may be approximated (for illustrative purposes) by the following equation.

$$\text{Pulse Pressure}(t) = \text{heart cycle}(t) * e^{(1/(AP-DBP))} \quad \text{Eq. 7}$$

where heart cycle (t) is the blood pressure of the user at any given time "t". The above Pulse Pressure equation (Eq. 7) is an approximation for illustrating the pulse pressure behavior when under an external applied pressure (AP), which contributes to the AC oscillatory effect described herein. The approximation or relationship can be described in other ways, such as with known equations using various parameters such as Young's Modulus (e.g., to describe vessel deformation) and/or other parameters, to describe the relationship which contributes to or creates the oscillatory effect, which is known and has been widely used in arm-cuff-based oscillatory BP measurement.

More specifically, as shown in FIG. 6C, the pulse pressure waveform 802 decreases to zero (or no oscillation) with increasing applied pressure. However, when the applied pressure 202 is substantially equal to the diastolic blood pressure (DBP) or the systolic blood pressure (SBP), the potential for oscillation measured by the force sensor 104, represented by the shaded area 804A, 804C of the pulse pressure waveform 802 beneath the applied pressure AP 202 horizontal line, is less than the potential for oscillation at the mean blood pressure (MBP), shown by the shaded area 804B. The applied pressure AP line 202 in the shaded area 804B is shown slightly above the "zero crossing" of the pulse pressure wave because the decay of the pulse pressure wave is non-linear (in this case, exponential), so the AP line will not be at the half-way (50%) point when AP=MBP.

As shown by the sensor readout curve 806 for the force sensor 104 (FIG. 1A), the sensor readout curve 806 exhibits oscillatory (or AC) pressure behavior (riding on a DC increasing applied pressure) between the diastolic blood pressure (DBP) and the systolic blood pressure (SBP), with an exhibited maximum average peak AC pressure oscillation value 216D substantially at the mean blood pressure (MBP).

Accordingly, we have found that we can calculate the mean blood pressure (MBP) of the user from peak of the pressure sensor oscillation plot 216, by measuring the AC component of the measured force signal from the force sensor 104. Measuring MBP enables user blood pressure SBP/DBP to be measured in various different ways, including, but not limited to, determining BP using the optical signal (e.g., PPG or photoplethysmography) from the finger and applied pressure (AP) signal caused by the finger pressure, and/or determining BP by measuring only the applied pressure (AP) caused by the finger pressure.

In particular, the device 10 may determine BP by measuring only the applied pressure (AP) caused by the finger pressure (and no optical source/sensor), by determining the MBP by sampling the digital pressure signal at a sufficient sample rate to be able to identify the AC components of the pressure (or pressure oscillation) near the frequency range of the heart rate (e.g., using a bandpass filter and AC maximum peak detector), and determining where the peak of the AC component occurs, which will correspond to the MBP (as described above). Once the MBP is determined, the blood pressure BP (i.e., SBP/DBP) may be determined (or approximated) by measuring at least one of DBP and SBP, as described herein, and obtaining the other from the below known relationship:

$$MBP=(DBP+SBP)/2 \qquad \text{Eq. 8}$$

The diastolic blood pressure (DBP) may be determined by the controller 112 based on the techniques discussed herein, e.g., when the optical signal begins to decrease in magnitude. Once the DBP is determined, the controller 112 may determine the systolic blood pressure (SBP) using Eq. 8 by knowing MBP and DBP. Similarly, the controller 112 may determine SBP using the optical curve fitting extrapolation techniques described hereinabove, which may then be used to determine DBP from Eq. 8.

In some embodiments, all three parameters may be determined, e.g., DBP and SBP from the optical technique described hereinabove, and MBP and/or DBP determined from the AC pressure oscillations (as described herein), and the values correlated to provide a quality or error check or continuous calibration of the device 10.

In some embodiments, the controller 112 may also determine DBP using pressure only (without using any optical source/sensor), by identifying when the pressure oscillation begins, i.e., when oscillation peak applied pressure is above DBP enough to measure the pressure oscillation by the force sensor 104. In that case, user blood pressure (BP) may be measured using only the force sensor 104 and no optical sensors. Also, if the pressure sensor has sufficient overall range to permit complete (or substantially complete) collapse of the vessel, SBP may be calculated by measuring where the pressure oscillations stop. In the above cases for measuring pressure oscillations, there may need to be a calibration offset or factor or adjustment that may be used to determine one or more of the values of MBP, DBP and SBP.

While some plots and values shown in the drawings herein are shown as being substantially linear or smooth, the actual values may fluctuate or be noisy and/or not follow a linear path. There may be fluctuating data due to, for example, sensitivity of the detecting components and unsteadiness of the user holding the BPM device 10 or unsteadiness in applying pressure. However, filtering or averaging the data may be performed to remove or reduce the effect of extraneous data points.

Figure 7:
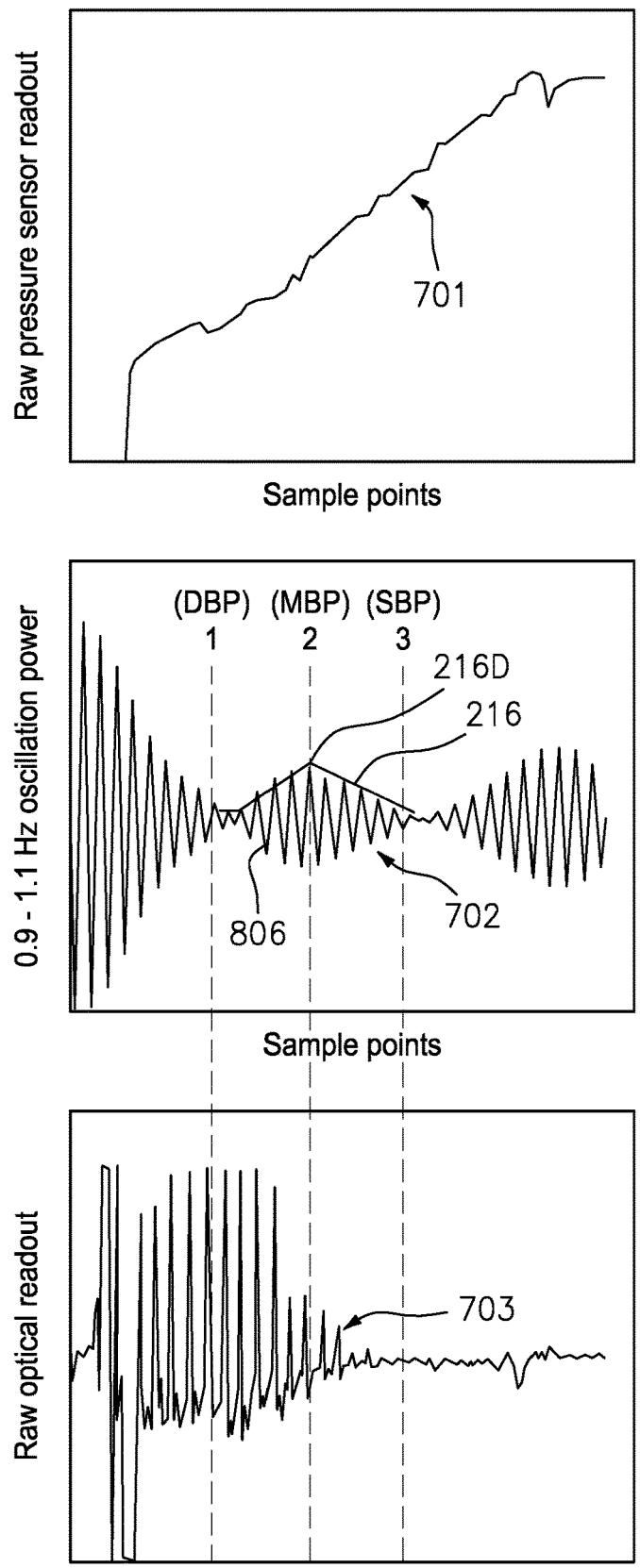
FIG. 7 shows sample data of applied pressure and pressure oscillation data detected at a force sensor of a blood pressure measuring device and raw optical readout detected at an optical sensor of the blood pressure measuring device in accordance with embodiments of the present disclosure.

Referring to FIG. 7, sample data is shown of actual recorded values 701 (or raw data) for the applied pressure AP as measured by the force sensor 104, pressure oscillation plot 702 detected by the force sensor 104 (FIG. 1A) and the optical reflectance 703 detected by the optical sensor 110 (FIG. 1B). The data may comprise a plurality of fluctuations or noise within the plots 701, 702, 703. Such fluctuations and/or noise may be "smoothed" out by the controller 112 (FIG. 1B) or be filtered by a digital or analog filter within the desired frequency bands of interest, e.g., a band pass filter, before the data/signals are transmitted to the controller 112. The band pass filter may be configured to allow (or pass) frequencies near heartbeat frequencies to pass through to the controller 112 (e.g., 0.90 to 1.05 Hz) or other frequencies may be used provided it gives the function and performance described herein. The applied pressure 202 shown as the raw measured curve 701 in FIG. 7 is increased continuously, but the principles of calculating blood pressure based on the collected data are the same as that described herein using pressure applied in steps or stages. In some embodiments, the applied pressure 202 may be applied in steps or stages, if desired.

Figure 8A:
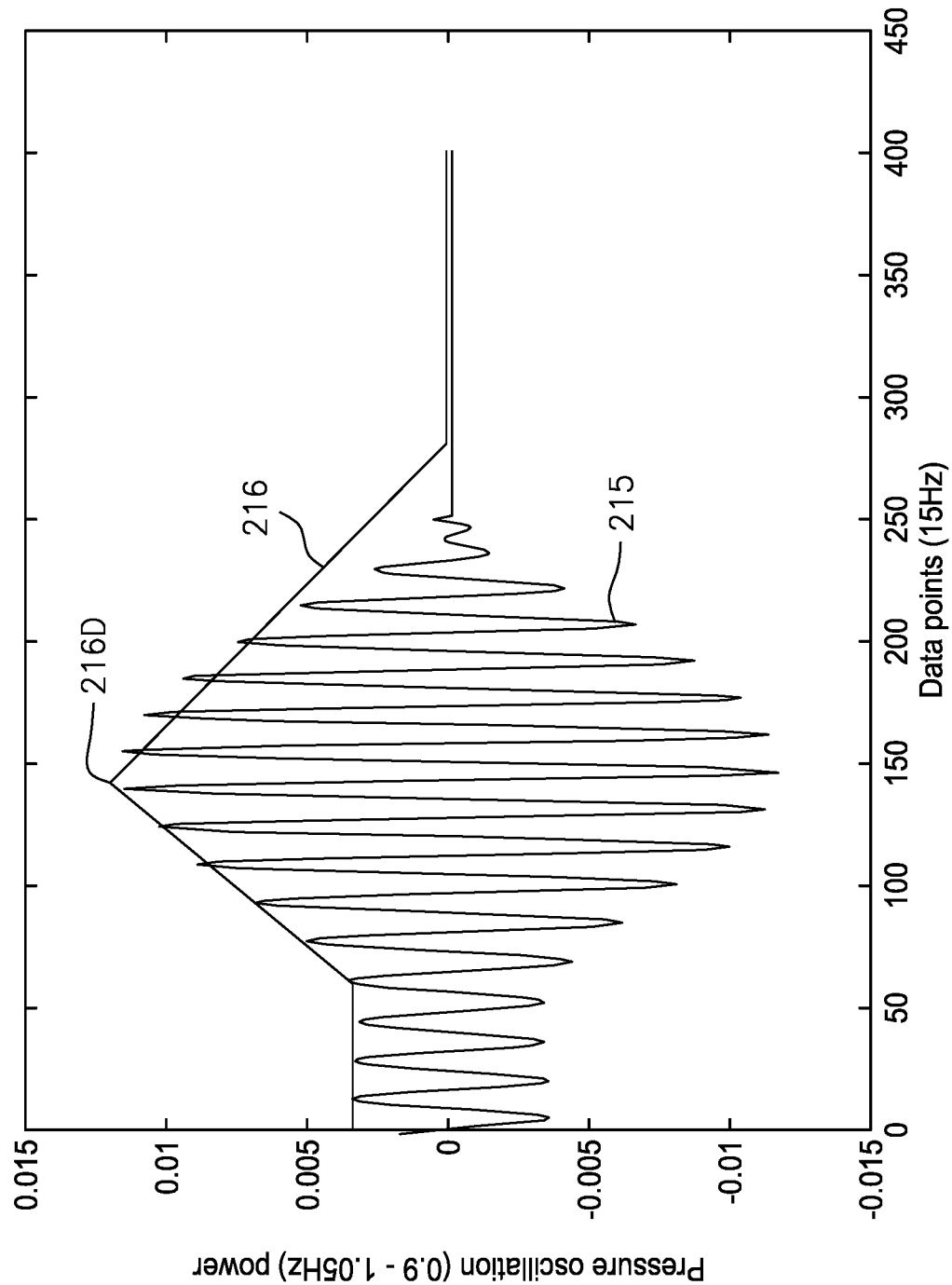
FIG. 8A is a sample plot of pressure oscillation data measured over time by a force sensor during the pressure applied resulting in the plot of FIG. 4A in accordance with embodiments of the present disclosure.
Figure 8B:
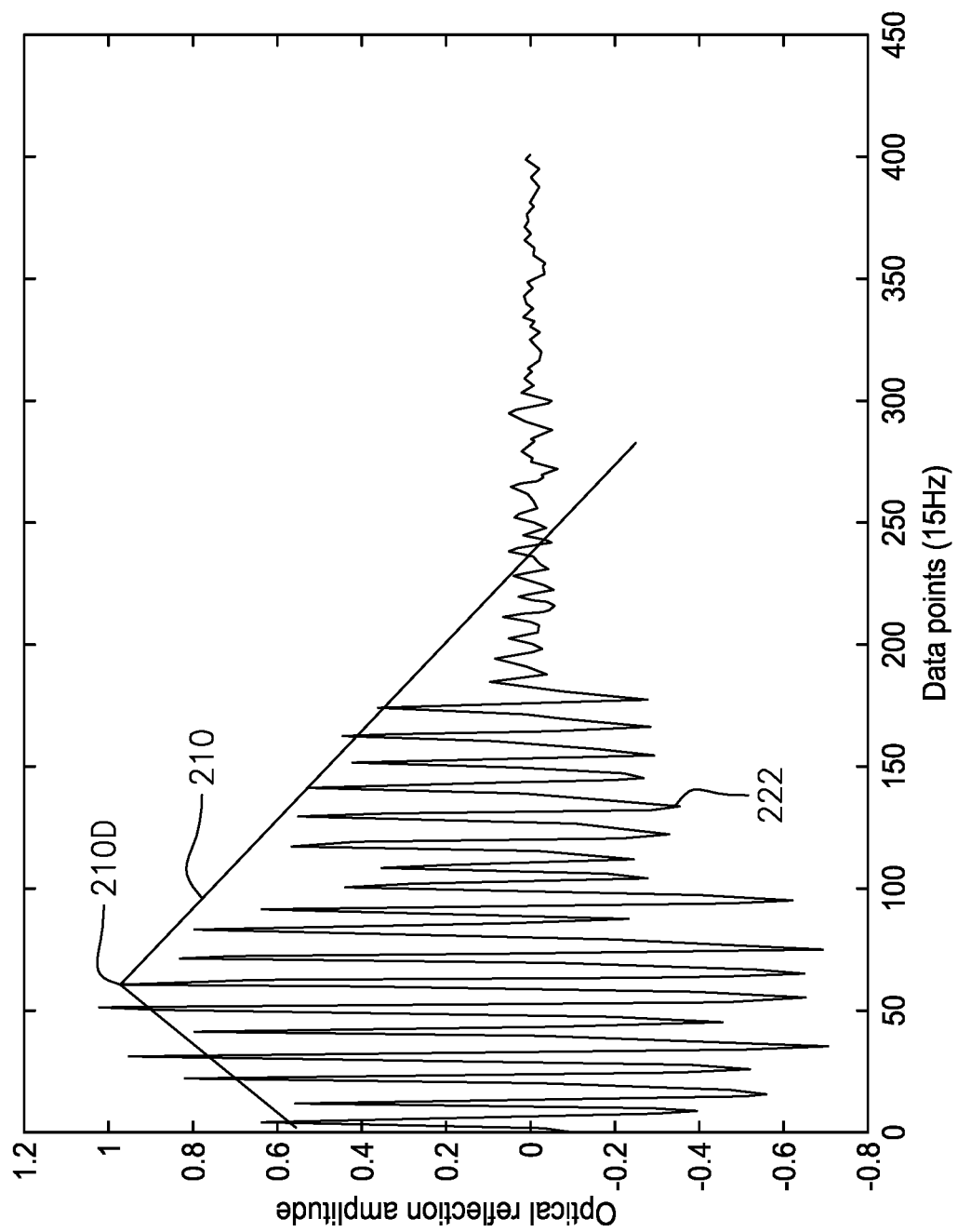
FIG. 8B is a sample plot of raw optical data collected by an optical sensor of a blood pressure measuring device collected during the data collection of FIG. 8A in accordance with embodiments of the present disclosure.

Referring to FIG. 8A, a plot of raw pressure oscillation data 215 collected during a pinching process of increasing applied pressure is plotted over a data collection frequency of 15 Hz. The maximum of the peaks of the pressure oscillation data 215 corresponds to the pressure oscillation plot 216 of FIG. 6A. Referring to FIG. 8B, raw optical reflection amplitude data collected during the pinching process of FIG. 8A is plotted. The peaks of the optical reflectance data 222 corresponds with the optical reflectance plot 210 of FIG. 2B.

Figure 9A:
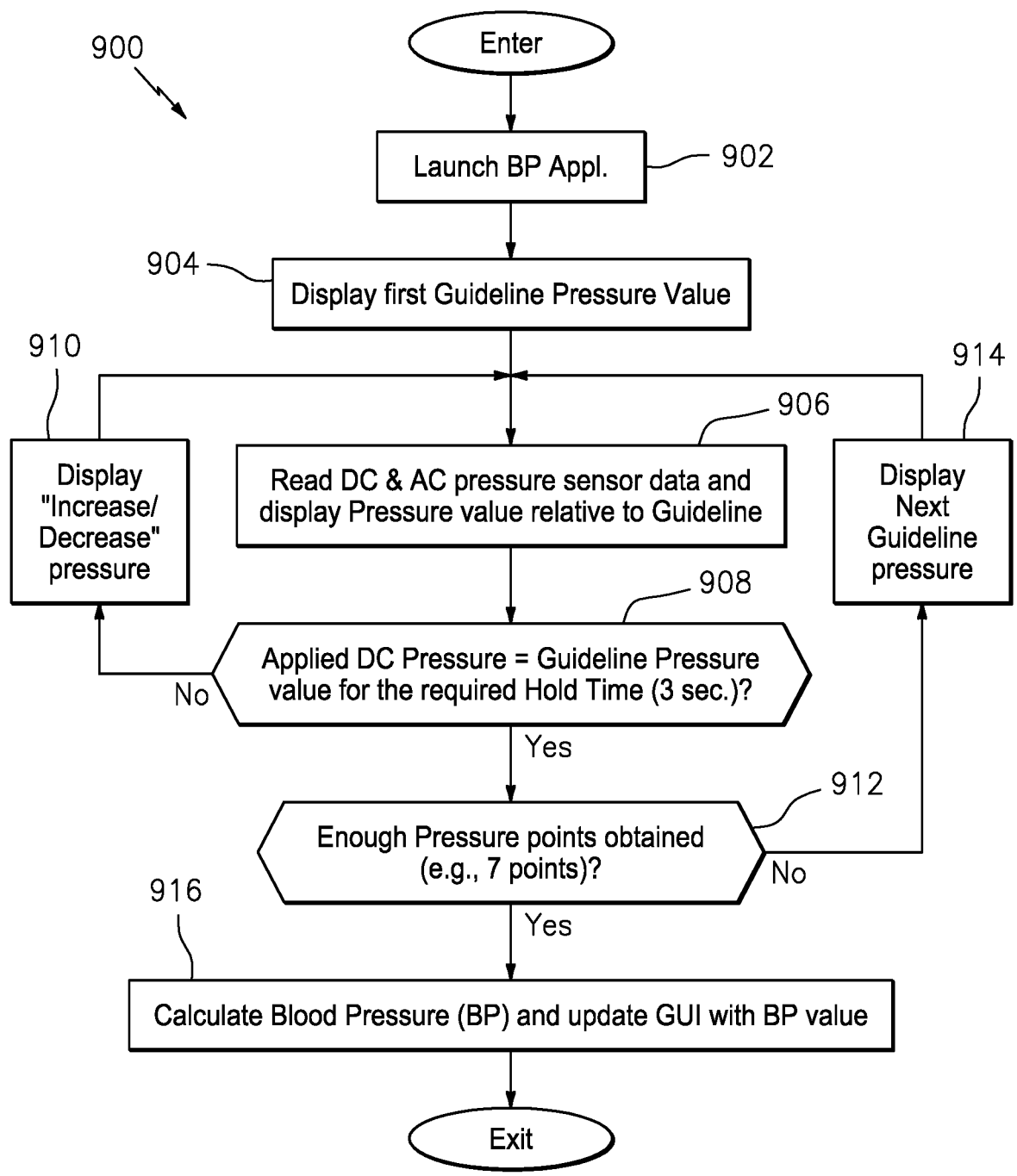
FIG. 9A is a flow diagram of a blood pressure measuring method being performed on a blood pressure measuring device in accordance with embodiments of the present disclosure.

Referring to FIG. 9A, a method flow diagram 900 of a blood pressure measurement method being performed on the device 10 of the present disclosure is shown. The method 500 begins at block 902, where a blood pressure measurement software application is launched on the smart phone. Then at block 904, a display screen of the device displays a first guideline pressure. Then at block 906, a force sensor (or pressure sensor) of the device reads DC and AC pressure sensor data being applied to the device and displays pressure value relative to the displayed first guideline. Then at block 908, the device determines whether the applied DC pressure is equal to the first guideline pressure within an upper and lower tolerance (or target or acceptable pressure range), e.g., +/−X force units (or pressure/psi or mmHg or other pressure units) of first guideline pressure value.

If the detected pressure is not within the tolerance of the first guideline pressure, then the method 900 proceeds to block 910 and displays an "increase pressure" notification if the detected pressure is less than the first guideline pressure and allotted lower tolerance or displays a "decrease pressure" notification if the detected pressure is greater than the first guidelines pressure and allotted upper tolerance. Then the method 900 returns to block 906.

If the detected pressure at block 908 is within the upper and lower tolerance (or acceptable range) of the first guideline pressure, then the method 900 proceeds to block 912 and the device determines whether enough data points were collected at enough guideline pressures, e.g., seven data points of seven different applied pressures at seven different guideline pressure values. Other number of pressure values or steps may be used if desired provided it provides the function and performance described herein. The pressure (or force) applied (or provided) by the user may in the form of pressure steps or stages, or may be a continuously increasing or decreasing applied pressure (or force).

In some embodiments, a continuously increasing or decreasing pressure may be applied by the users finger over a predetermined range sufficient to make the measurements discussed herein, such as that shown in the curve 701 in FIG. 7, or the applied pressure curve 202 in FIG. 6C, and which may be displayed to the user in real-time, may be used with any of the embodiments described herein.

If the determined number of data points at block 912 is less than a predetermined number of data points, the method 900 proceeds to block 914 and displays the next guideline pressure on the display screen of the device. The method 900 is then repeated for blocks 906-912 with the exception that the next guideline pressure is used instead of the first guideline pressure.

If the determined number of data points at block 912 is greater than or equal to a predetermined number of data points, the method 900 proceeds to block 916 and the device calculates blood pressure and updates the graphical user interface ("GUI") with a blood pressure value (discussed hereinafter). Then the method 900 exits.

Figure 9B:
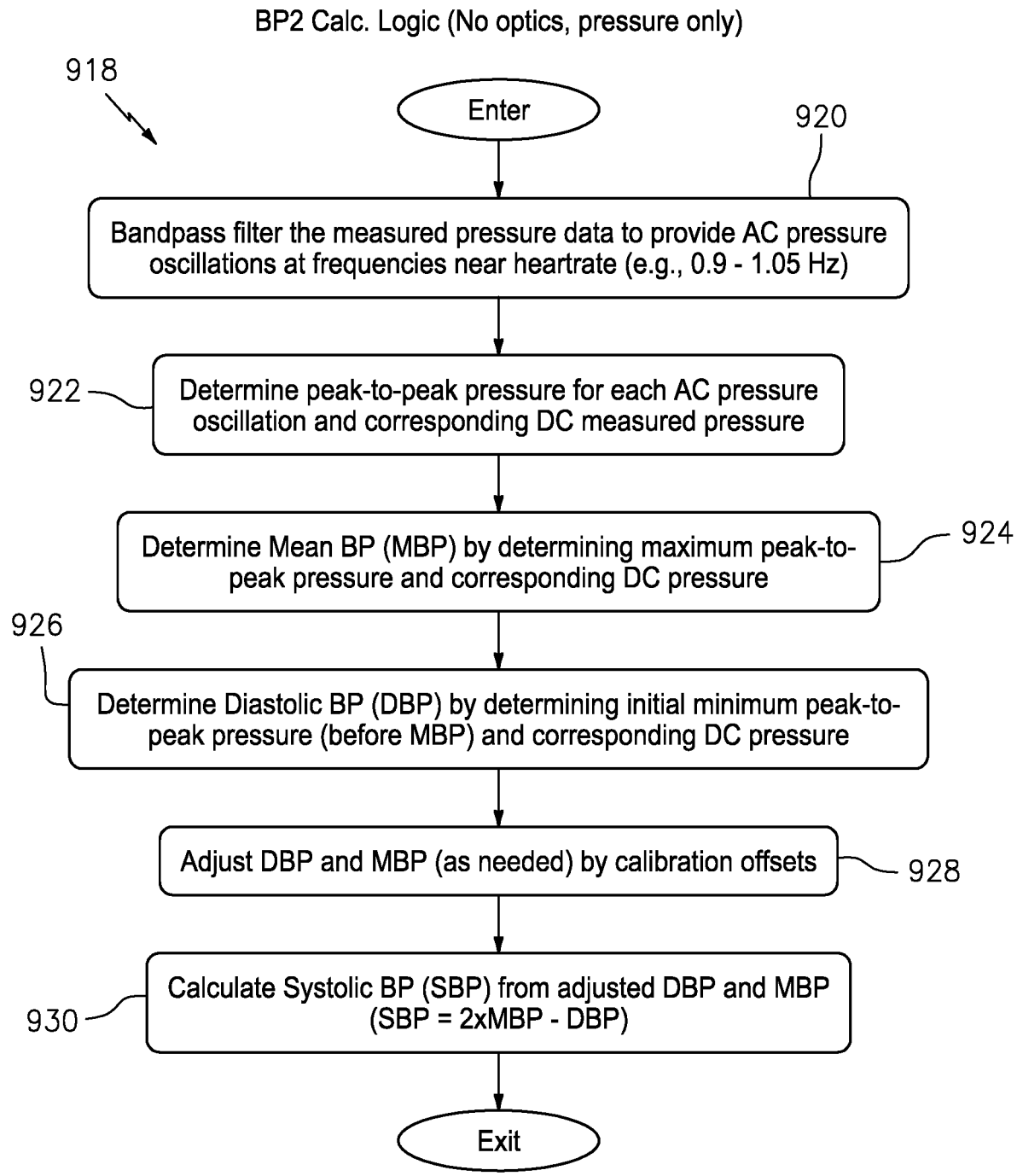
FIG. 9B is a flow diagram of a portion of the blood pressure measuring method of FIG. 9A in accordance with embodiments of the present disclosure.

Referring to FIG. 9B, an exemplary method flow diagram 918 is shown for performing the calculation of blood pressure at block 916 (FIG. 9A). The process 918 begins at block 920 where measured pressure data from the force sensor 104 is filtered through a bandpass filter to provide AC pressure oscillations at frequencies near the expected user heartrate. For example, the bandpass filter may allow pressure oscillation data in the frequency range of 0.90 to 1.05 Hz. Other bandpass frequency ranges and types of filters may be used if desired, provided it provides the function and performance described herein. Then at block 922, the device determines peak-to-peak pressure for each AC pressure oscillation and corresponding DC measured pressure. Then at block 924, the device determines an initial mean blood pressure (MBP) value by determining the maximum peak-to-peak pressure and corresponding DC pressure. Then at block 926, the device determines an initial diastolic blood pressure value (DBP) by determining a minimum peak-to-peak pressure (before MBP peak if applied pressure applied in increasing manner or after MBP peak if applied pressure applied in decreasing manner) and corresponding DC pressure. Then at block 928, the device adjusts the diastolic blood pressure (DBP) and/or mean blood pressure (MBP) values (as needed) by corresponding calibration adjustments or offsets. The calibration adjustments or offsets may be predetermined for the device based on empirical data to adjust the determined periphery blood pressures to determined central blood pressures by a transformation function such as, for example, a linear transformation, or any other transformation that provides the desired accuracy. Then at block 930, the device calculates systolic blood pressure (SBP) from the adjusted diastolic blood pressure (DBP) and mean blood pressure (MBP) values according to the equation SBP=(2*MBP)−DBP. Then the process 918 exits. The calibration adjustments for DBP and MBP may be any type of respective adjustment(s) or equation(s) specific for that parameter (DBP,MBP) that provides the desired calibration results for the respective parameter (DBP,MBP). The calibration may be performed in another portion of the process if desired, provided it provides the desired results or accuracy.

Figure 10:
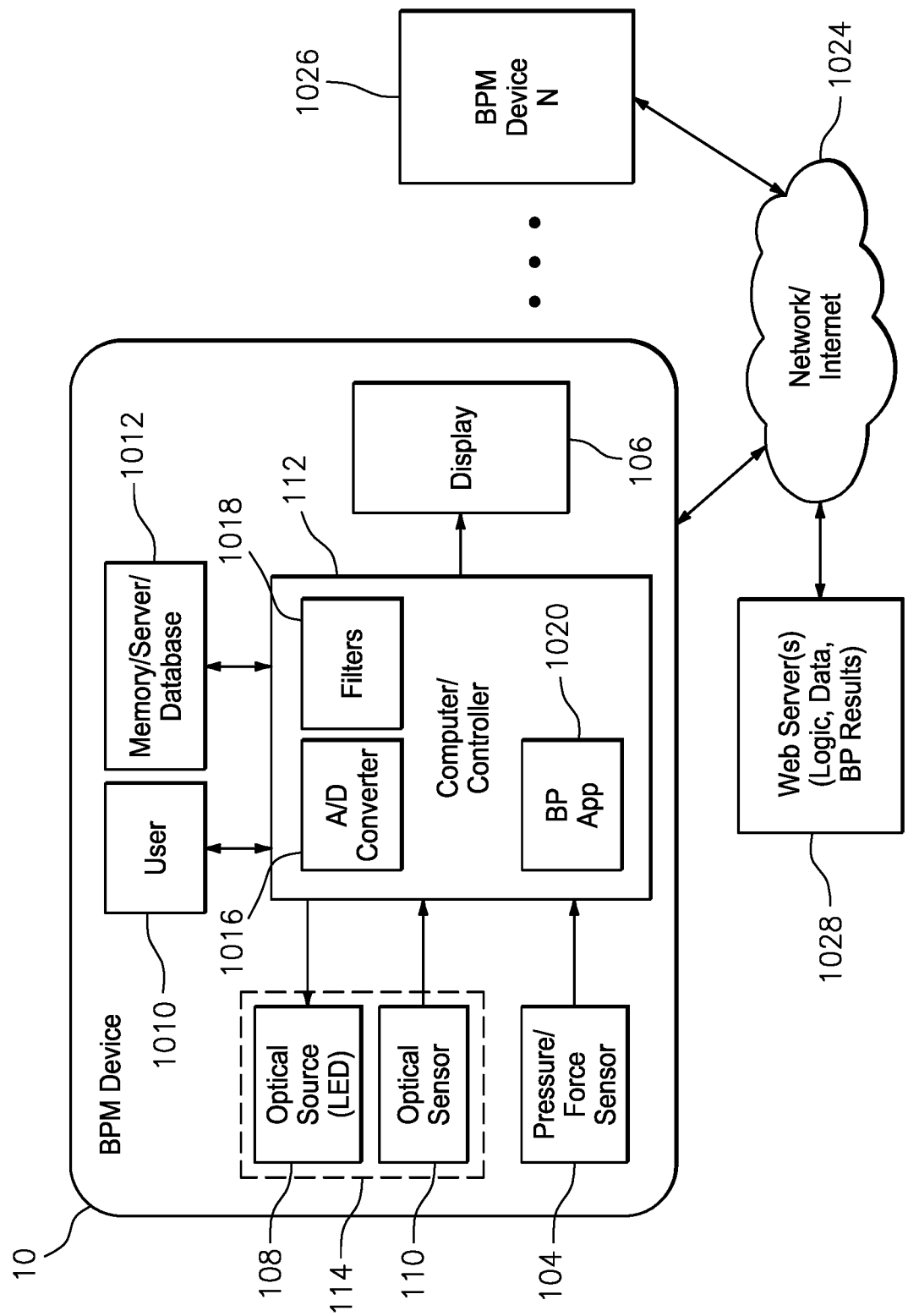
FIG. 10 is a system diagram of a blood pressure measuring system in accordance with embodiments of the present disclosure.

Referring to FIG. 10, a block diagram of the BP measurement Device 10 is shown, including the controller 112 (FIG. 1B) which communicates with the light source 108, the optical sensor 110, and pressure/force sensor 104, as described herein with FIGS. 1A, 1B, 1C. The controller 112 may be a computer or computer-based device or component(s) that can perform the functions described herein. The controller 112 also may receive input commands from the user 1010, and may store data to or retrieve data from memory or server or database 1012.

The controller 112 may also communicate with the display 106 (FIG. 1A) to provide instructions to the user 1010 or (if touch sensitive) receive commands, data, and other inputs from the user 1010, as described herein. The controller 112 may also have an on-board analog-to-digital converter (A/D converter or ADC) 1016, digital and/or analog filters 1018, and any other appropriate or necessary interfaces and/or signal conditioning required to provide the functions described herein. The controller 112 may also have software for performing the functions described herein such as the BP Software Application (or BP App) 1020 running on the computer or controller 112, as described herein. For embodiments herein that do not require the optical source/sensor arrangement 114, the device 10 need not have these features or sensors.

As described herein, the user 1010 interacts with the device 10 and the device 10 controls the light source 108 and reads the optical sensor 110 and pressure sensor 104 and performs calculations described herein to perform the blood pressure measurement or other measurements as described herein and may provide feedback or notifications and may display the results on the display 106 to the user 1010, or may send the results over a network 1024 to a web site or smart phone for access or use by the user 1010 or medical professionals or others. The BPM device 10 may also communicate with the network 1024 (e.g., the interne or other network) and other BPM Devices 1026 may also be connected to the network 1024 and may store or access results, data or logic from a network server 1028, which may also be accessed through the network 1024 by medical professionals for health monitoring purposes. Also, the BP App 1020 may be located on the controller or stored in the device memory 1012 or located remotely on a local server or network/web-based server 1028 or other server/storage device. As described herein, the device 10 may be implemented using a smart phone, such as an iPhone® made by Apple Inc. or other smart phone or smart device or any other computer-based device or collection of components, hardware, firmware and software, that can perform the functions described herein.

Figure 11:
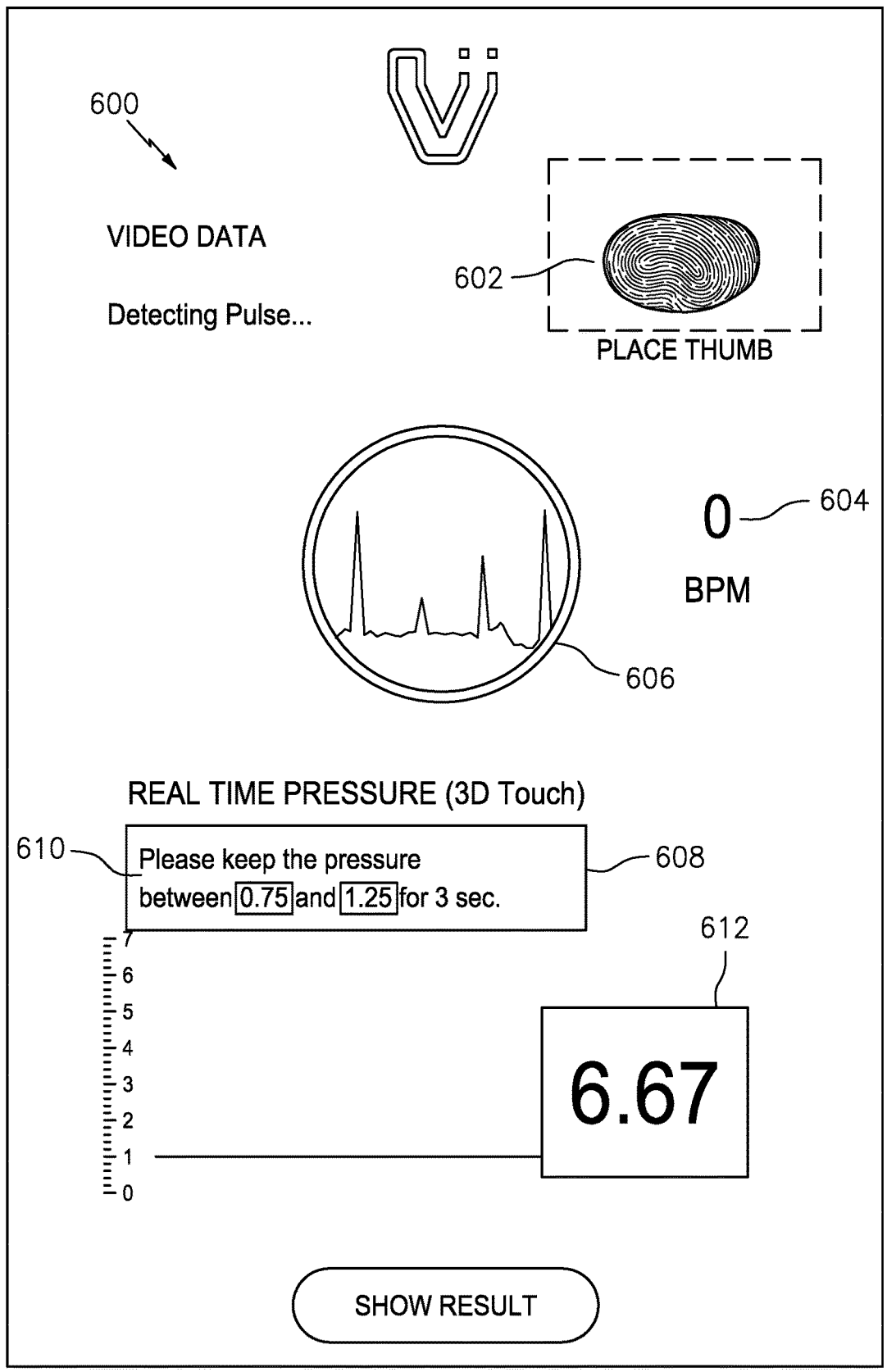
FIG. 11 is a depiction of a graphical user interface of a blood pressure measuring device in accordance with embodiments of the present disclosure.

Referring to FIG. 11, a graphical user interface 600 of a blood pressure measuring device 10 is shown. The graphical user interface is configured to be displayed on the display screen 106 of the device 10. The graphical user interface 600 includes a thumb print indicator 602. However, a finger print indicator for any finger may be used in place of the thumb print indicator 602. The thumb print indicator 602 is displayed on the display screen 106 so that pressure applied by a user's thumb, or other finger, at the area of the display screen 106 showing the thumb print indicator will be detected by the force sensor 104. A heart rate indicator 604 (BPM) displays a real-time heart rate detection. A visual heart rate graphic 606 depicts the heart rate of the user and/or the intensity of the detected heart beats as detected by the force sensor 104. The graphical user interface 600 further includes a dialogue box 608 that includes written instructions 610 for the user. The written instructions 610 may change as the pinching process progresses and/or if the user needs to repeat steps for completion of the blood pressure detection method. An applied pressure indicator 612 depicts real-time applied pressure 202 of the user at the thumb print indicator 602. The instructions 610 in the dialogue box 608 may provide instructions for the user to vary or maintain the applied pressure so that the pressure indicated at the applied pressure indicator 612 remains within a predetermined range for a predetermined amount of time, as discussed above in connection with the pinching process. Alternatively, the instructions 610 may instruct the user to increase or decrease the applied pressure 202 at a certain rate.

In some embodiments, the force sensor 104 (or pressure sensor) may be a film pressure sensor including a variable resistor that changes its resistance in a log-linear manner when pressure is applied. The photo detector of the optical sensor 110 may be configured to generate a voltage signal based on the amount of light reflected from the user's finger, which will change with each heartbeat. The user's pulse can be recorded at the user's index finger (or other finger) during the pinching process in accordance with embodiments of the present disclosure.

In some embodiments, the applied pressure area value of the finger of the user used by the controller 112 in the equation Pressure=Force/Area will be a constant value. In some embodiments, the applied pressure area value will be estimated based on characteristics of the user such as, for example, age, height, weight and/or gender. In some embodiments, the controller 112 is able to approximate an applied pressure area value based on an array force values detected by the force sensor 104.

Figure 12:
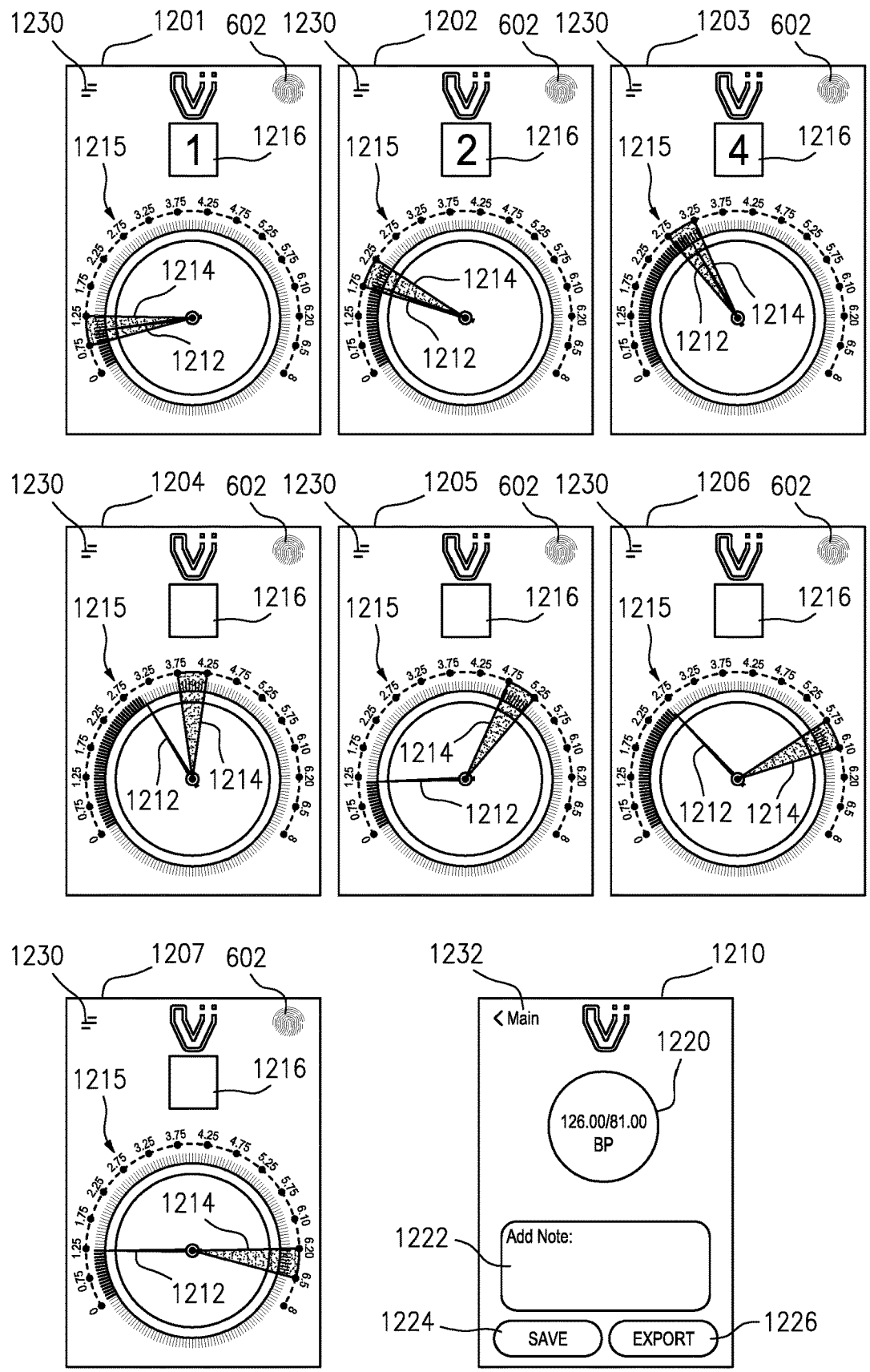
FIG. 12 is a series of screen illustrations of a user interface of a blood pressure measuring device showing pressure measurement screens and BP results screen, in accordance with embodiments of the present disclosure.

Referring to FIG. 12, a plurality of pressure/force reading screen illustrations (or pressure meter screens) 1201-1207 are shown for a series of seven (7) increasing pressure readings (each screen having an illustration of a pressure or force meter 1215, a timer/counter 1216, and the finger print region 602 showing the user where to apply pressure), and a BP results screen 1210 showing the resulting blood pressure measurement is shown. The below table shows the acceptable pressure ranges (or tolerance) for the seven (7) pressure levels shown in FIG. 12. The force meter 1215 shows a plurality of force units (ranging from 0 to 8 force units) around the perimeter of the circular meter 1215, which correspond to signal values received from the force/pressure sensor. Other geometric shapes, e.g., rectangular or other shapes, for the force meter 1215 may be used if desired. Other units for the meter may be displayed if desired, e.g., pressure units in psi or mmHg (using the conversion described with Eq. 2 herein). Other tolerances may be used if desired, provided it provides the function and performance described herein.

| Pressure Level (or step) | Acceptable pressure/force range (force units) |
| --- | --- |
| 1 | 0.75-1.25 |
| 2 | 1.75-2.25 |
| 3 | 2.75-3.25 |
| 4 | 3.75-4.25 |
| 5 | 4.75-5.25 |
| 6 | 5.75-6.10 |
| 7 | 6.20-6.5 |

In this embodiment, the device screen displays the pressure meter 1215 which has a pressure meter needle 1212 which responds to pressure (or force) applied to the touch-sensitive screen (or pressure or force sensor) and a target or acceptable pressure range "wedge" 1214 (or tolerance) for each pressure level (or step). When pressure is applied to the screen at the location 602, the needle moves in a clockwise direction for increasing pressure and a counter-clockwise direction for decreasing pressure. When the applied pressure is within the desired pressure wedge 1214, a hold timer (or counter) 1216 at the top of the screen is displayed and decrements from 5 seconds in 1 second increments until it gets to zero (0). When the timer 1216 gets to zero, the screen displays the next pressure wedge 1214, shown in the next successive screen illustration 1202, 1203, 1204, 1205, 1206, 1207, respectively, associated with the next pressure state or level. If the needle goes outside the wedge 1214, the timer 1216 turns off (displays no number) as shown in screens 1204-1207, and will restart from 5 seconds again when the needle returns to inside the wedge 1214 for a given pressure level. In some embodiments, if the pressure or optical readings when inside the tolerance wedge 1214 are acceptable, and the needle exits and then re-enters the wedge 1214 before the timer reaches 0, the timer may continue counting down from where it left-off when the needle moved outside the wedge 1214. This process is repeated for the seven (7) pressure levels as shown. Other number of levels and tolerance ranges may be used if desired, as discussed herein. Any other display screens may be used if desired to provide the user with feedback regarding the applied pressure (or force) and tolerances.

After the last pressure level is completed, the screen automatically displays BP results screen 1210, showing the user's blood pressure, having a results region 1220, and may also provide a notes region 1222 for the user to type in any information about the reading that may be relevant, e.g., "performed after eating breakfast". The results screen 1210 may also have a Save button 1224 to save the BP results, and an Export button 1226 to export the results to a desired destination, server, device or third party (e.g., doctor's office).

In some embodiments, the backlighting of the screen 1201-1207 may be one color (e.g., to green) when the needle 1212 is within the acceptable tolerance pressure wedge 1214, and change to a different color (e.g., red), when the needle is outside the acceptable pressure wedge 1214. In some embodiments, there may be vibration or haptic or audio feedback provided to the user to indicate when the pressure needle 1212 enters or exits the pressure wedge 1214.

The pressure/force tolerances shown herein are for ease of use by the user during the multi-step BP measurement process and do not result in corresponding to errors or tolerances on the resulting output blood pressure BP measurement.

Also, in some embodiments, the pressure meter screens 1201-1207 may be the "Main" screen, and there may be a drop-down menu button 1230 which may provide a list of options for the user, such as "Start", "History", "How to Use", "Privacy Policy", "Logout". Further, in some embodiments, the BP results screen 1210 may have a "Main" button 1232, which, when selected (or pressed or clicked on) brings the user back to the Main screen with the pressure meter 1215. In some embodiments, for best accuracy, the finger being measured should be held substantially at the height of the heart of the user.

While the pinching process has been shown and described as a user applying a plurality of different force levels in a step-wise fashion. It is within the scope of the present disclosure for the pinching process to be in accordance with other types of increasing force patterns. For example, the pinching process may be a continuous increase where the user increases the applied pressure increases at a constant rate (linear) or non-constant rate (non-linear). Alternatively, the applied pressure changes can be done in a decreasing manner, either in stages or substantially continuously.

In some embodiments, there may be more than one light source 108 and/or more than one optical sensor 110. Other configurations are also contemplated and discussed herein. The optical sensor 110 may be configured to take a plurality of pictures in order to obtain the optical reflectance data discussed herein. The plurality of pictures may be taken at various frequencies such that the plurality of pictures constitute video data in the sense that the plurality of pictures resemble a video when viewed in sequence.

In some embodiments, the force sensor 104 and display screen 106 may be configured together as an integrated piezo resistive pixelated touch sensitive display such as that in a smart phone, such as an Apple iPhone® 6S or equivalent. The iPhone 6S "3D Touch" force sensor technology may be used to detect applied force by a user and pressure oscillations in the applied force as discussed above. The force sensor or touch sensitive display may also be used to determine the digitally pixelated touch area of the finger used to apply the pressure if desired, which may be used in the pressure calculation discussed hereinafter. Any other type of force sensors or pressure sensors that enables trackpads or touchscreens to distinguish between various levels of force being applied to their surfaces may be used provided it provides the sufficient force measurement sensitivity to perform the measurements discussed herein.

In some embodiments, the controller 112 can be an Arduino controller, or any other controller capable of performing the functions described herein. For example, the controller 112 can be a controller associated with the Arduino Uno Rev3 microcontroller board (microcontroller ATmega328P by Atmel®).

While specific notification schemes are described herein, other notification schemes are within the scope of the present disclosure. For example, notifications may be generated by the blood pressure detection apparatus 10 to instruct the user to begin applying pressure at the next applied pressure level, or notifications may be continuously, or intermittently, generated at the intended applied pressure level and then cease when it is time to instruct the user to begin applying the appropriate pressure at the next applied pressure level.

The blood pressure detection apparatuses and methods described herein have generally referred to a single finger pinching from one side of an apparatus and a single finger pinching from a different side of the apparatus (or device 10). However, it is within the scope of the present disclosure for more than one finger pinching from one side of the apparatus and/or more than one finger pinching from a different side of the apparatus. For example, two fingers may be pinching from one side of the apparatus and two different fingers may be pinching at a different side of the apparatus, or three fingers may be pinching from one side of the apparatus and one finger may be pinching from a different side of the apparatus. In such embodiments, multiple fingers may be pinching a single force sensor and single optical source/sensor configuration 114, or there may be separate force sensors and/or light source/optical sensor configurations 114 for each pinching finger of the user. Also, the fingers on each side of the device may be from different hands if desired.

Also, in some embodiments there may be only a single finger pressing from only one side of the apparatus, e.g., when the pressure and optical sensors/sources are facing out of (or located on or interact with) the same (single) side of the device, or when the force or pressure sensor (on the opposite side of the device or in a sandwich-type structure between two opposite sides) is placed against a solid non-flexible surface (provided the force sensor measures (or is related to) the force applied by the finger onto the optical sensor/sources). In some embodiments, the optical source/sensors may be located behind the display, and the force/pressure sensor may be a force/pressure-sensitive display or may be a sensor located at any location where the device can detect the applied force on the finger and provide a force signal indicative thereof to the device.

The BPM device 10 of FIGS. 1A-1C have the force sensor 104 on opposite sides of the device 10 from the optical source/sensor configuration 114. However, it is within the scope of the present disclosure to have the force sensor 104 and optical source/sensor configuration 114 on the same side of the device 10. For example, the force sensor 104 may be arranged adjacent to the optical source/sensor configuration 114, or the light source/optical sensor configuration 114 may be arranged within or underneath a surface of the force sensor 104, or the light source/optical sensor configuration 114 may integrated with the force sensor 104 such that the pressure/force sensor 104 and light source/optical sensor 114 both interact with the user's finger on the same side (a single side) of the device 10.

Also, in some embodiments, the sensors/sources 104, 114 that interact with the finger (or fingers) may be located on one or two sides of a separate sensing device 150 (FIG. 1A), which may be attached to the main device 10 by a connection or cord 152, which connects to the device 10 with a connector/plug/port 154 (e.g., USB, micro-USB, HDMI, lightning, or any other connector that provided the necessary signals to provide the desired functions herein), or, in some embodiments, the connection 152 may be a wireless connection. In that case, the sensing device 150 provides sensor signals (e.g., voltage) indicative of the measured parameters, e.g., applied force sensed by the force sensor 104 and/or optical reflection signal as sensed or received by the optical (or light) detector, to the main device 10, e.g., the controller 112 in the device 10, for processing the sensor signals as described herein. The sensing device 150 may also receive power from the main device 10 or from a battery in the sensing device 150 or by another source. The sensing device 150 has the necessary hardware, firmware and/or software to perform the functions described herein. The device 10 as used herein, may refer to the main device 10 and the sensing device 150, collectively, and may include any other peripheral sensing or display devices or components connected thereto necessary to perform the functions described herein. In some embodiments, the sensing device 150 may also include the controller 112 or portions of the controller 112, and/or the display 106 which may be on one or both the main device 10 and the sensing device 150. In some embodiments, the sensing device 150 may be a sensing plate, having the force sensor 104, that lays on a surface or table and the user presses a finger on the plate, as directed by the main device 10, to produce the desired force and the main device 10 provides the resulting blood pressure (BP) results via the display 106 and/or electronically via text, email, SMS or other electronic wired or wireless transmission. In that case, the main device may be a smart phone or other computer-based device having the necessary hardware and software to communicate with the sensing device and to display or otherwise provide feedback to the user regarding applied pressure and target tolerances and/or BP results.

Also, the device 10 or the sensing device 150 may be integrated into or configured as a "wearable" device, such as a watch (or "smart watch"), e.g., an Apple Watch Series 5 made by Apple Inc., or equivalent smart watch having a force/pressure-sensitive screen that can detect applied force/pressure with the sensitivity over the desired force/pressure range to perform the functions described herein, or body-worn activity monitor, body-worn health monitor (or the like), or bracelet or necklace, or any article or item or clothing that is wearable or attachable to any portion of the body and can be pressed by at least one finger of the user.

In that case, the wearable device may have the components and sensors discussed herein in the main device 10, or the wearable device may have a portion of the components and sensors discussed herein in the main device 10 and the rest of the components may be in a remote device (e.g., smart phone, laptop, tablet, or other computer-based device), which communicates with the wearable device. For example, in some embodiments, if the device 10 is a wearable item or device (e.g., a watch or smart watch), the watch may contain the pressure and/or optical sensors and display, and any needed electronics, and the watch may transmit the sensed data to the remote device, for processing and/or calculating the BP results, and then the watch may receive the BP results from the remote device to display BP results to the user, or the remote device may display the BP results. In some embodiments, the remote device may have a display that provides visual feedback in real-time to the user for tracking the force applied by the user's finger (e.g., steps or continuous increasing/decreasing force and tolerances), and in some embodiments, the wearable device may have components that provide real-time feedback to the user by providing vibrations (or tactile), sounds, and/or visual display to the user from the wearable device. In some embodiments, the wearable display, which may be partially or mostly covered by the finger applying the force, may illuminate a color that is visible around the applying finger and may provide color-coded guidance or color in combination with vibration (or tactile) and/or sounds.

For example, in some embodiments the main device 10 may be a smart phone (e.g., an Apple iPhone or equivalent) and the remote sensing device 150 may be a smart watch (e.g., an Apple Watch or equivalent). In that case, the smart watch would receive the pressure from the finger and the smart phone would provide the display for the user to read the applied pressure, target pressure tolerance for each pressure level, and time at each pressure level within the tolerance, and display the resulting blood pressure (BP) measurement value, e.g., 120/80. In addition, if using both optical and pressure measurements, the user may remove or loosen the Apple Watch and pinch the watch, similar to pinching the smart phone described hereinbefore, such that the user's thumb presses on the watch display and an opposing finger (e.g., index finger or other opposing finger) is covering the optical source/sensor on the back side of the smart watch—for watches that do not have optical sensors on the upper surface behind the display.

In some embodiments, if the optical source/sensor can sense blood in a blood vessel of the wrist and the vessel compresses with applied pressure to the watch face, the user blood pressure (BP) may be determined from the technique described herein. In that case, the user may only need to apply pressure to the face of the watch (using any controllable force applying mechanism, such as the opposite hand or other body part or object), for the pressure levels and hold times as described herein to obtain the user blood pressure.

The optical sensor may be configured to detect light in narrow or wide ranges of wavelengths of light. For example, the optical sensor may be configured to detect light in the 300 nm-700 nm wavelength range, or in a different wavelength range, such as in a green color wavelength range of 520 nm-560 nm, which is more stable than other wavelength ranges. For example, the optical sensor may be a Pulse Sensor (part no. SEN-11574) sold by Karlsson Robotics and configured to be used with an Arduino device. However, optical sensors configured to detect other light wavelength ranges are in within the scope of the present disclosure. A constant multiplier may be applied to the optical data obtained from the optical sensor depending on operating parameters of the optical sensor, such as, for example, the wavelength range the optical sensor is configured to detect and the light intensity the optical sensor is configured to detect.

Advantageously, blood pressure detection apparatuses and methods according to the present disclosure are not limited to a device designed as solely a "dedicated" blood pressure detection device. Specifically, the blood pressure detection apparatus may be implemented using other devices. For example, the blood pressure detection apparatus can be a smart phone, a camera or a music player. For example, the blood pressure detection apparatus or BPM device 10 may be an iPhone 6S. If for example the BPM device 10 is a smart phone, such as an iPhone made by Apple, Inc., the force sensor 114 may be arranged beneath or within the touchscreen of the smart phone and the optical sensor 110 may be a camera of the phone for taking pictures or videos and the light source 108 may be a flash light bulb of the device. Other force sensors are within the scope of the present disclosure. For example, the force sensor 104 may be a Force Sensitive Resistor (part no. SEN-09375) having a diameter of 0.5" as sold by SparkFun Electronics.

Advantageously, blood pressure detection apparatuses and methods according to the present disclosure are able to detect a blood pressure of a user from a finger of the user without an optical sensor. Thus, based on the determined periphery blood pressure, a central blood pressure determination can be made.

As will be recognized by those of ordinary skill in the pertinent art, numerous modifications and substitutions can be made to the above-described embodiments of the present disclosure without departing from the scope of the disclosure. Accordingly, the preceding portion of this specification is to be taken in an illustrative, as opposed to a limiting, sense.

Although the disclosure has been described herein using exemplary techniques, algorithms, or processes for implementing the present disclosure, it should be understood by those skilled in the art that other techniques, algorithms and processes or other combinations and sequences of the techniques, algorithms and processes described herein may be used or performed that achieve the same function(s) and result(s) described herein and which are included within the scope of the present disclosure.

Any process descriptions, steps, or blocks in process or logic flow diagrams provided herein indicate one potential implementation, do not imply a fixed order, and alternate implementations are included within the scope of the preferred embodiments of the systems and methods described herein in which functions or steps may be deleted or performed out of order from that shown or discussed, including substantially concurrently or in reverse order, depending on the functionality involved, as would be understood by those reasonably skilled in the art.

It is noted that the Figures are to be taken as an illustrative examples only, and are not to scale, unless otherwise indicated herein.

It should be understood that, unless otherwise explicitly or implicitly indicated herein, any of the features, characteristics, alternatives or modifications described regarding a particular embodiment herein may also be applied, used, or incorporated with any other embodiment described herein.

Conditional language, such as, among others, "can," "could," "might," or "may," unless specifically stated otherwise, or otherwise understood within the context as used, is generally intended to convey that certain embodiments could include, but do not require, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

The devices 10 described herein and shown in FIGS. 1A-1C and 10 may be a computer-controlled device having the necessary electronics, computer processing power, interfaces, memory, hardware, software, firmware, logic/state machines, databases, microprocessors, communication links, displays or other visual or audio user interfaces, printing devices, and any other input/output interfaces, including sufficient optics and optical control and measurement capability and pressure or force measurement capability, to provide the functions or achieve the results described herein. Except as otherwise explicitly or implicitly indicated herein, process or method steps described herein are implemented within software modules (or computer programs) executed on one or more general purpose computers. Specially designed hardware may alternatively be used to perform certain operations. In addition, computers or computer-based devices described herein may include any number of computing devices capable of performing the functions described herein, including but not limited to: tablets, laptop computers, smart phones, desktop computers and the like.

Although the invention has been described and illustrated with respect to exemplary embodiments thereof, the foregoing and various other additions and omissions may be made therein and thereto without departing from the spirit and scope of the present disclosure.

What is claimed is:

1. A blood pressure measurement apparatus, comprising:
    an optical source/sensor disposed on the apparatus and arranged to receive a first finger of a user the first finger having a blood vessel disposed therein, the optical source/sensor providing an optical source signal incident on the first finger and receives a reflected optical signal from the first finger related to blood volume in the blood vessel, and the optical source/sensor providing an optical reflection signal indicative of the blood volume;
    a force sensor disposed on the apparatus, arranged to measure applied pressure by the finger on the optical source/sensor, the force sensor providing an applied pressure signal indicative of the applied pressure to the blood vessel; and
    a controller operatively connected to the optical source/sensor and the force sensor and configured to receive the optical reflection signal and the applied pressure signal and configured to determine a blood pressure of the user based on the applied pressure signal and the optical reflection signal using a plurality of optical reflection signals corresponding to a plurality of applied pressures to the first finger of the user, the plurality of applied pressures defining an applied pressure range;
    wherein the apparatus provides feedback to the user of target applied pressures and actual applied pressures needed to calculate the user blood pressure;
    wherein the force sensor detects AC pressure oscillations exerted against the force sensor by the first finger of a user based on heartbeats of the user and the applied pressure signal is also indicative of the AC pressure oscillations;
    wherein the controller is configured to provide an AC pressure oscillation signal based on the applied pressure signal at frequencies near a heart rate of the user, and determines the peak-to-peak pressure for the AC pressure oscillations over the applied pressure range; and
    wherein the controller is further configured to calculate a mean blood pressure (MBP) by determining a maximum peak-to-peak pressure over the applied pressure range, and to calculate the DBP by determining an initial minimum peak-to-peak pressure before the MBP occurs and a corresponding applied pressure, and calculating SBP by the equation: SBP=2×MBP−DBP.

2. The apparatus of claim 1, wherein the plurality of applied pressures comprises a plurality of pressure levels, the number of levels comprising at least one of: 3, 4, 5, 6, 7, 8, 9, and 10.

3. The apparatus of claim 1, wherein the plurality of applied pressures comprises the applied pressure being held for at least a predetermined hold time, the hold time comprising one of: 1 second, 2 seconds, 3 seconds, 4 seconds, 5 seconds, 6 seconds, 7 seconds, 8 seconds, 9 seconds, and 10 seconds.

4. The apparatus of claim 1, wherein the controller calculates an average optical pulse peak-to-peak height as an average optical height for each pressure level.

5. The apparatus of claim 4, wherein the controller calculates the diastolic BP (DBP) by determining the maximum of the average optical heights for all pressure levels as a maximum average optical height.

6. The apparatus of claim 5, wherein the controller calculates systolic blood pressure (SBP) by curve fitting the average optical heights starting from the maximum average optical height as the fitted curve; determine an extrapolated optical data point multiplying an extrapolation factor by the maximum average optical height; and determine SBP by inserting the extrapolated optical data point into the fitted curve.

7. The apparatus of claim 6, wherein the fitted curve comprises an exponential curve fit.

8. The apparatus of claim 6, wherein the extrapolation factor is about 30%.

9. The apparatus of claim 6, wherein the controller adjusts DBP by a DBP calibration offset to determine actual DBP and adjusts SBP by an SBP calibration offset to determine actual SBP.

10. The apparatus of claim 1, further comprising a display screen operatively connected to the controller and the controller displays on the screen the force being applied to the optical source/sensor.

11. The apparatus of claim 2, wherein the plurality of applied pressure levels each have a corresponding acceptable pressure tolerance to be within to start a hold timer, the hold timer providing the feedback of the hold time to the user.

12. The apparatus of claim 1, wherein the feedback comprises at least one of: visual, haptic/touch, and audio.

13. The apparatus of claim 1, wherein the apparatus is configured to receive a second finger which applies a second force against the apparatus which is related to the force applied by the first finger against the optical source/sensor.

14. The apparatus of claim 13, wherein the second finger comprises a thumb and the first finger is an opposing finger to the thumb on the same hand of the user, and the first finger comprises one of: index finger, middle finger, ring finger, and little/pinky finger.

15. The apparatus of claim 1, wherein the apparatus comprises a smart phone, the optical source/sensor comprises a controllable digital camera with a controllable flash and the pressure sensor comprises a touch-screen display.

16. The apparatus of claim 1, wherein the apparatus comprises a smart watch, the optical source/sensor comprises a controllable digital camera with a controllable flashlight and the pressure sensor comprises a touch-screen display.

17. The apparatus of claim 1, wherein the plurality of applied pressures comprises a plurality of pressure steps, each pressure step being held within a predetermined pressure tolerance for a predetermined hold time.

18. The apparatus of claim 1, wherein the plurality of applied pressures comprises continuously increasing or decreasing pressures between a first pressure value and a second pressure value, the first pressure value and second pressure value defining the applied pressure range.

19. A blood pressure measurement apparatus, comprising:
an optical source/sensor disposed on the apparatus and arranged to receive a first finger of a user the first finger having a blood vessel disposed therein, the optical source/sensor providing an optical source signal incident on the first finger and receives a reflected optical signal from the first finger related to blood volume in the blood vessel, and the optical source/sensor providing an optical reflection signal indicative of the blood volume;
a force sensor disposed on the apparatus, arranged to measure applied pressure by the finger on the optical source/sensor, the force sensor providing an applied pressure signal indicative of the applied pressure to the blood vessel; and
a controller operatively connected to the optical source/sensor and the force sensor and configured to receive the optical reflection signal and the applied pressure signal and configured to determine a blood pressure of the user based on the applied pressure signal and the optical reflection signal using a plurality of optical reflection signals corresponding to a plurality of applied pressures to the first finger of the user, the plurality of applied pressures comprises a plurality of pressure steps defining an applied pressure range, each pressure step being held within a predetermined pressure tolerance for a predetermined hold time;
wherein the apparatus provides feedback to the user of target applied pressures and actual applied pressures needed to calculate the user blood pressure;
wherein the force sensor detects AC pressure oscillations exerted against the force sensor by the first finger of a user based on heartbeats of the user and the applied pressure signal is also indicative of the AC pressure oscillations;
wherein the controller is configured provide an AC pressure oscillation signal based on the applied pressure signal at frequencies near a heart rate of the user, and determines the peak-to-peak pressure for the AC pressure oscillations over the applied pressure range; and
wherein the controller is further configured to calculate a mean blood pressure (MBP) by determining a maximum peak-to-peak pressure over the applied pressure range, and to calculate the DBP by determining an initial minimum peak-to-peak pressure before the MBP occurs and a corresponding applied pressure, and calculating SBP by the equation: SBP=2×MBP−DBP.

20. A blood pressure measurement apparatus, comprising:
an optical source/sensor disposed on the apparatus and arranged to receive a first finger of a user the first finger having a blood vessel disposed therein, the optical source/sensor providing an optical source signal incident on the first finger and receives a reflected optical signal from the first finger related to blood volume in the blood vessel, and the optical source/sensor providing an optical reflection signal indicative of the blood volume;
a force sensor disposed on the apparatus, arranged to measure applied pressure by the finger on the optical source/sensor, the force sensor providing an applied pressure signal indicative of the applied pressure to the blood vessel; and
a controller operatively connected to the optical source/sensor and the force sensor and configured to receive the optical reflection signal and the applied pressure signal and configured to determine a blood pressure of the user based on the applied pressure signal and the optical reflection signal using a plurality of optical reflection signals corresponding to a plurality of applied pressures to the first finger of the user, the plurality of applied pressures comprising continuously increasing or decreasing pressures between a first pressure value and a second pressure value, the first pressure value and second pressure value defining an applied pressure range;
wherein the apparatus provides feedback to the user of target applied pressures and actual applied pressures needed to calculate the user blood pressure;
wherein the force sensor detects AC pressure oscillations exerted against the force sensor by the first finger of a user based on heartbeats of the user and the applied pressure signal is also indicative of the AC pressure oscillations;
wherein the controller is configured to provide an AC pressure oscillation signal based on the applied pressure signal at frequencies near a heart rate of the user, and determines the peak-to-peak pressure for the AC pressure oscillations over the applied pressure range; and
wherein the controller is further configured to calculate a mean blood pressure (MBP) by determining a maximum peak-to-peak pressure over the applied pressure range, and to calculate the DBP by determining an initial minimum peak-to-peak pressure before the MBP occurs and a corresponding applied pressure, and calculating SBP by the equation: SBP=2×MBP−DBP.

* * * * *